United States Patent
Yerramilli et al.

(10) Patent No.: US 10,775,365 B2
(45) Date of Patent: Sep. 15, 2020

(54) HOMOGENOUS IMMUNOASSAY WITH COMPENSATION FOR BACKGROUND SIGNAL

(71) Applicant: IDEXX Laboratories, Inc., Westbrook, ME (US)

(72) Inventors: Murthy V S N Yerramilli, Falmouth, ME (US); Hongzhi Xie, Falmouth, ME (US); Daniel Wayne Patch, Portland, ME (US); Giosi Farace, Georgetown, ME (US)

(73) Assignee: IDEXX LABORATORIES, Inc., Westbrook, ME (US)

(*) Notice: Subject to any disclaimer, the term of this patent is extended or adjusted under 35 U.S.C. 154(b) by 330 days.

(21) Appl. No.: 15/048,209

(22) Filed: Feb. 19, 2016

(65) Prior Publication Data

US 2016/0245801 A1 Aug. 25, 2016

Related U.S. Application Data

(60) Provisional application No. 62/118,832, filed on Feb. 20, 2015.

(51) Int. Cl.
*G01N 33/53* (2006.01)
*C12N 9/04* (2006.01)
*G01N 33/542* (2006.01)
*G01N 33/68* (2006.01)

(52) U.S. Cl.
CPC ....... *G01N 33/5308* (2013.01); *C12N 9/0006* (2013.01); *G01N 33/542* (2013.01); *G01N 33/6812* (2013.01); *C12Y 101/01049* (2013.01); *G01N 2800/347* (2013.01)

(58) Field of Classification Search
CPC .......... C12N 9/0006; C12Y 101/01049; G01N 2800/347; G01N 33/5308; G01N 33/542
See application file for complete search history.

(56) References Cited

U.S. PATENT DOCUMENTS

| | | | |
|---|---|---|---|
| 3,875,011 | A | 4/1975 | Rubenstein et al. |
| 4,485,177 | A | 11/1984 | Siedel et al. |
| 4,686,181 | A | 8/1987 | Dona |
| 4,818,703 | A | 4/1989 | Pizzolante |
| 5,318,680 | A | 6/1994 | Fishman et al. |
| 5,726,010 | A | 3/1998 | Clark |
| 6,358,699 | B1 | 3/2002 | Balint et al. |
| 6,455,288 | B1 | 9/2002 | Jakobovitis et al. |
| 6,699,673 | B2 | 3/2004 | Aletta |
| 6,720,188 | B2 | 4/2004 | Kaddurah-Daouk et al. |
| 6,736,957 | B1 | 5/2004 | Forrow et al. |
| 6,706,742 | B2 | 10/2004 | De Nanteuil et al. |
| 7,611,844 | B2 | 11/2009 | Lin et al. |
| 8,481,690 | B2 | 7/2013 | Murthy et al. |
| 9,091,684 | B2 | 7/2015 | Yerramilli et al. |
| 9,970,927 | B2 * | 5/2018 | Yerramilli ............. C07C 279/12 |
| 2004/0242723 | A1 | 8/2004 | Yerramilli et al. |
| 2004/0214252 | A1 | 10/2004 | Lin et al. |
| 2005/0266574 | A1 | 12/2005 | Kosaka |
| 2006/0094122 | A1 | 5/2006 | Boeger et al. |
| 2006/0201805 | A1 | 9/2006 | Forrow et al. |
| 2010/0035274 | A1 * | 2/2010 | Murthy ................. C07C 279/12 435/7.1 |
| 2012/0129265 | A1 | 5/2012 | Lundin et al. |
| 2013/0280740 | A1 | 10/2013 | Yerramilli et al. |
| 2014/0221616 | A1 * | 8/2014 | Donahue ............ G01N 33/5308 530/367 |
| 2014/0242723 | A1 * | 8/2014 | Yerramilli ............. C07C 279/12 436/501 |
| 2019/0120856 | A1 * | 4/2019 | Xie ..................... G01N 33/6812 |

FOREIGN PATENT DOCUMENTS

| | | |
|---|---|---|
| EP | 1666884 | 6/2006 |
| WO | 1998/49199 | 11/1998 |
| WO | 2002/014873 | 2/2002 |
| WO | 2004/046314 | 6/2004 |
| WO | 2006/078813 | 7/2006 |
| WO | 2007/074864 | 7/2007 |
| WO | 2010/017089 | 2/2010 |
| WO | 2015/035155 | 3/2015 |

OTHER PUBLICATIONS

A printout retrieved from http://www.science.uwaterloo.ca/~cchieh/cact/c120/bondel.html on Apr. 23, 2018.*
A printout P1709 retrieved from https://www.sigmaaldrich.com/catalog/product/sigma/p1709?lang=en&region=US on Apr. 23, 2018.*
A printout SIA (succinimidyl iodoacetate) retrieved from https://www.thermofisher.com/order/catalog/product/22349 on Apr. 23, 2018.*
Englebienne, "Immune and Receptor Assays in Theory and Practice," CRC Press, 2000, p. 308.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Sopio et al., "Reaction of 3-deoxypentosulose with N-methyl- and N, N-dimethylguanidine as model reagents for protein-bound arginine and for creatine," Z. Lebensm. Unters Forsch. A., 1995, pp. 381-386, vol. 201.
Stuhlinger et al., "Relationship Between Insulin Resistance and an Endogenous Nitric Oxide Synthase Inhibitor," J. Am. Med. Assoc., 2002, pp. 1420-1426, vol. 287, No. 1.

(Continued)

*Primary Examiner* — Galina M. Yakovleva
(74) *Attorney, Agent, or Firm* — McDonnell Boehnen Hulbert & Berghoff LLP

(57) ABSTRACT

Homogeneous immunoassays that allow for compensation of background signals inherent in samples and reagents. The use of homogeneous immunoassays for the detection of the presence or amount of symmetrical Dimethyl Arginine (SDMA) in biological samples. Reagents and kits for conducting the assays.

6 Claims, 12 Drawing Sheets

(56) References Cited

OTHER PUBLICATIONS

Szurdoki et al., "Important Factors in Hapten Design and Enzyme-Linked Immunosorbent Assay Development," Immunoanalysis of Agrochemicals, ACS Symposium Series, American Chemical Society, 1995, pp. 39-63, Chapter 4, vol. 586.

Takahashi, Kenji, "The Reaction of Phenylglyoxal with Arginine Residues in Proteins," J. Biol. Chem., Dec. 10, 1968, pp. 6171-6179, vol. 243, No. 23.

Teerlink et al., "Determination of Arginine, Asymmetric Dimethylarginine, and Symmetric Dimethylarginine in Human Plasma and Other Biological Samples by High-Performance Liquid Chromatography," Anal. Biochem., 2002, pp. 131-137, vol. 303.

Upstate cell signaling solutions, "Certificate of Analysis for Anti-dimethyl-Arginine, symmetric (SYM10)," rabbit polyclonal IgG; downloaded May 24, 2011 from www.millipore.com, 2 pages.

Upstate cell signaling solutions, "Certificate of Analysis for Anti-dimethyl-Arginine, symmetric (SYM11)," rabbit polyclonal IgG; downloaded May 24, 2011 from www.millipore.com, 2 pages.

Vanholder et al., Review on uremic toxins: Classification, concentration, and interindividual variability, Kidney International, May 1, 2003, pp. 1934-1943, vol. 63.

Vishwanathan et al., "Determination of arginine and methylated arginines in human plasma by liquid chromatography-tandem mass spectrometry," Journal of Chromatography B, 2000, pp. 157-166, vol. 748.

Hall et al., "Comparison of Serum Concentrations of Symmetric Dimethylarginine and Creatinine as Kidney Function Biomarkers in Cats with Chronic Kidney Disease," J Vet Intern Med (2014), 28:1676-1683.

Opiate 200 Ng (OP2) Chemistry Information Sheet, Aug. 2010, Beckman Coulter Inc.

COCM Chemistry Information Sheet, Aug. 2010, Beckman Coulter Inc.

Emit® 2000 Carbamazepine Chemistry Information Sheet, Sep. 2010, Beckman Coulter Inc.

Emit® 2000 Vancomycin Chemistry Information Sheet, Sep. 2010, Beckman Coulter Inc.

"ADMA—ELISA, Enzyme Immunoassay for the quantitative Determination of Endogenous Asymmetric Dimethylarginine (ADMA) in Serum or Plasma (Instruction for use)," Diagnostika GMBH, Apr. 2007, 16 pages.

Baburaj, K. et al., "HOCGO and DMACGO. Two coumarin derived alpha-dicarbonyls suitable as pH and polarity sensitive fluorescent reporters for proteins that can be targeted at reactive arginines," Biochim. Biophys. Acta, 1994, pp. 253-265, vol. 1199.

Bedford et al., "Arginine Methylation: An Emerging Regulator of Protein Function," Mol. Cell, 2005, pp. 263-272, vol. 18.

Biovendor Research and Diagnostic Products: "Enzyme Immunoassay for the Quantitative Determination of Endogenous Symmetric Dimethylarginine (SDMA) on Serum or Plasma", SDMA ELISA, Instructions for use, 2008, 13 pages.

Blackwell et al., "Biological variation of asymmetric dimethylarginine and related arginine metabolites and analytical performance goals for their measurement in human plasma," European Journal of Clinical Investigation, 2007, pp. 364-371, vol. 37.

Bode-Böger et al., "Symmetrical Dimethylarginine: A New Combined Parameter for Renal Function and Extent of coronary Artery Disease," Journal of the American Society of Nephrology, 2006, pp. 1128-1134, vol. 17.

Bode-Böger, S.M. et al., "Elevated L-Arginine/Dimethylarginine Ratio Contributes to Enhanced Systemic NO Production by Dietary L-Arginine in Hypercholesterolemic Rabbits," Biochem. Biophys. Res. Commun., 1996, pp. 598-603, vol. 219.

Böger, Rainer, "Asymmetric dimethylarginine (ADMA): A novel risk marker in cardiovascular medicine and beyond," Annals of Medicine, 2006, pp. 126-136, vol. 38.

Boisvert et al., A Proteomic Analysis of Arginine-Methylated Protein Complexes, Molecular & Cellular Proteomics, 2003, pp. 1319-1330, vol. 2, No. 12.

Boisvert, Francois-Michel, "A Role for Arginine Methylation in DNA Repair," Dissertation abstracts International, 2005, 234 pages.

Boisvert et al., "Symmetrical dimethlyarginine methylation is required for the localization of Snm in Cajal bodies and pre-mRNA splicing", J. Biol. Chem., Dec. 23, 2002, pp. 957-969, vol. 59, No. 6.

Brahms et al., "The C-terminal RG Dipeptide Repeats of the Spliceosomal Sm Proteins D1 and D3 contain Symmetrical Dimethylarginines, Which Form a Major B-cell epitope for Anti-Sm Autoantibodies," The Journal of Biological Chemistry, 2000, pp. 17122-17129, vol. 275, No. 22.

Chen et al., "Determination of NG, NG-dimethylarginine in human plasma by high-performance liquid chromatography," Journal of Chromatography B, 1997, pp. 467-471, vol. 692.

Cooper et al. "Cyclic Forms of the alpha-Keto Acid Analogs of Arginine, Citrulline, Homoarginine, and Homocitrulline," J. Biol. Chem., Aug. 10, 1978, pp. 5407-5410, vol. 253, No. 15.

Dobashi et al., "An automated analyzer for methylated arginines in rat plasma by high-performance liquid chromatography with post-column fluorescence reaction," Analyst, 2002, pp. 54-59, vol. 127.

Duerksen, P.J. et al., Immobilization of Proteins Via Arginine Residues, Anal. Biochem., 1987, pp. 444-454, vol. 160.

Duncan et al., "A New Reagent Which may be Used to Introduce Sulfhydryl Groups into Proteins, and Its use in the Preparation of Conjugates for Immunoassay," Analytical Biochemistry, 1983, pp. 68-73, vol. 132.

Finco, et al., "Relationship between plasma creatinine concentration and glomerular filtration rate in dogs," Journal of Veterinary Pharmacology and Therapeutics, 1995, pp. 418-421, vol. 18.

Fleck et al., "Serum concentrations of asymmetric (ADMA) and symmetric (SDMA) dimethylarginine in renal failure patients," Kidney International, 2001, pp. 14-18, vol. 59, No. 78.

Fliser et al., "Asymmetric Dimethylarginine and Progression of Chronic Kidney Disease: The Mild to Moderate Kidney Disease Study," Journal of the American Society of Nephrology, 2005, pp. 2456-2461, vol. 16.

Goodrow et al., "Strategies for Immunoassay Hapten Design," Immunoanalysis of Agrochemicals, ACS Symposium Series, American Chemical Society, 1995, pp. 119-139, Chapter 9, vol. 586.

Greene, T.W. et al., "Chapter 5—Protection for the Carboxyl Group," Protective Groupsin Organic Synthesis, 3rd Edition, 1999, pp. 369-453.

Greene, T.W. et al., "Chapter 6—Protection for the Thiol Group," Protective Groupsin Organic Synthesis, 3rd Edition, 1999, pp. 454-493.

Greene, T.W. et al., "Chapter 7—Protection for the Amino Group," Protective Groupsin Organic Synthesis, 3rd Edition, 1999, pp. 494-653.

Kielstein et al., "Symmetric dimethylarginine (SDMA) as endogenous marker of renal function—a meta-analysis," Nephrol Dialysis Transplantation, 2006, pp. 2446-2451, vol. 21.

Kitagawa et al., "Preparation and Characterization of Hetero-Bifunctional Cross-linking Reagents for Protein Modificiations," Chem. Pharm. Bull, 1981, pp. 1130-1135, vol. 29, No. 4.

Koch et al., "Regulation and Prognostic Relevance of Symmetric Dlmethylarginine Serum Concentrations in Critical Illness and Sepsis," Mediators of Inflammation, Jun. 27, 2013, pp. 1-8, vol. 2013.

Levey et al., "Glomerular filtration rate measurements in clinical trials. Modification of Diet in Renal Disease Study Group and the Diabetes Control and Complications Trial Research Group." Journal of the American Society of Nephrology, 1993, pp. 1159-1171, vol. 4, No. 5.

Liu et al., "New procedures for preparation and isolation of conjugates of proteins and a synthetic copolymer of D-amino acids and immunochemical characterization of such conjugates," Biochemistry, 1979, pp. 690-697, vol. 18, No. 4.

MacAllister et al., "Concentration of dimethyl-L-arginine in the plasma of patients with end-stage renal failure," Nephrology Dialysis Transplantation, Dec. 11, 1996, pp. 2449-2452, vol. 11.

(56) References Cited

OTHER PUBLICATIONS

Mahler et al., "Identification of a SmD3 epitope with a single symmetrical dimethylation of an arginine residue as a specific target of a subpopulation of anti-Sm antibodies," Arthritis Research & Therapy, 2004, pp. R19-R29, vol. 7, No. 1.

Midttun et al., "High-throughput, low-volume, multianalyte quantification of plasma metabolites related to one-carbon metabolism using HPLC-MS/MS," Analytical and Bioanalytical Chemistry, Dec. 13, 2012, pp. 2009-2017, vol. 405.

Moesgaard et al., "Effects of breed, gender, exercise and white-coat effect on markers of endothelial function in dogs," Research in Veterinary Science, 2007, pp. 409-418, vol. 82.

Nabity et al., "Day-to-Day Variation of the Urine Protein: Creatinine Ratio in Female Dogs with Stable Glomerular Proteinuria Caused by X-Linked Hereditary Nephropathy," J. Vet. Intern. Med., 2007, pp. 425-430, vol. 21.

Nijveldt et al., "Handling of asymmetrical dimethylarginine and symmetrical dimethylarginine by the rat kidney under basal conditions and during endotoxaemia," Nephrol Dial. Transplant, 2003, pp. 2542-2550, vol. 18.

Ogawa et al., "Metabolism of NG, NG- and NG, N'G-Dimethylarginine in rats," Arch. Biochem. Biophys., Feb. 1, 1987, pp. 526-537, vol. 252, No. 2.

Palmer et al., "Reduction and Reoxidation of a Critical Disulfide Bond in the Rabbit Antibody Molecule," J. Biol. Chem., 1963, pp. 2393-2398, vol. 238, No. 7.

Perrone et al., "Utility of Radioisotopic Filtration Markers in Chronic Renal Insufficiency: Simultaneous Comparison of 125I-Iothalamate, 169Yb-DTPA, 99mTc-DTPA, and Inulin," Am. J. Kidney Disease, 1990, pp. 224-235, vol. 16, No. 3.

Peterson et al., "Using Hapten Design to Discover Therapeutic Monoclonal Antibodies for Treating Methamphetamine Abuse," The Journal of Pharmacology and Experimental Therapeutics, 2007, pp. 30-39, vol. 322, No. 1.

Pettersson et al., Determination of dimethylated arginines in human plasma by high-performance liquid chromatography, Journal of Chromatography B, 1997, pp. 257-262, vol. 692.

Pi et al., "Improved method for simultaneous determination of L-arginine and its mono- and dimethylated metabolites in biological samples by high-performance liquid chromatography," Journal of Chromatography B, 2000, pp. 199-203, vol. 742.

Pravetoni et al., "Structurally distinct nicotine immunogens elicit antibodies with non-overlapping specificities," Biochemical Pharmacology, 2012, pp. 543-550, vol. 83, No. 4.

Product Information List, DLD Diagnostika GmbH, retrieved online www.dld-diagnostika.de/produkt_en.php?id=52, Jan. 25, 2011, 2 pages.

Richard et al., "Arginine methylation regulates IL-2 gene expression: a role for protein arginine methyltransferase 5 (PRMT5)," Biochem J., 2005, pp. 379-386, vol. 388.

Schnabel et al., "Asymmetric Dimethylarginine and the Risk of Cardiovascular events and Death in Patients with Coronary Artery Disease—results from the AtheroGene Study," Circulation Research, 2005, pp. 1-7, vol. 97.

Schulze et al., "Determination of asymmetric dimethylarginine (ADMA) using a novel ELISA assay," Clin. Chem. Lab Med., 2004, pp. 1377-1383, vol. 42, No. 12.

Schulze et al., "Determination of a reference value for NG, NG-dimethyl-L-arginine in 500 subjects," European Journal of Clinical Investigation, 2005, pp. 622-626, vol. 35.

Schwarzenbolz, U. et al., "On the reaction of glyoxal with proteins," Zeitschrift für Lebensmitteluntersuchung and - Forschung A, 1997, pp. 121-124, vol. 205.

SDMA (human) ELISA kit, Enzo Life Sciences, Version 01: Dec. 8, 2009, 19 pages.

SDMA—ELISA, "Instructions for Use; Enzyme Immunoassay for the quantitative Determination of Endogenous Symmetric Dimethylarginine (SDMA) in Serum or Plasma," DLD Diagnostika GMBH, Feb. 2008, 16 pages.

The Extended European Search Report for PCT/US2016/018667 dated Jul. 6, 2018, pp. 1-11.

Batch D. et al. "Abstract B-47 High Throughput Immunoassay for Kidney Function Biomarker Symmetric Dimethylarginine (SDMA)" Clin Chern (2015) pp. 3-3. XP055487566—Retrieved from the Internet: URL:https://www.aacc.org/science-and-practice/annual-meeting-abstracts-archive/2015-annual-meeting-abstracts [retrieved on Jun. 25, 2018].

* cited by examiner

FIG. 5 Mediator-Dye Reaction Mechanism

FIG. 9
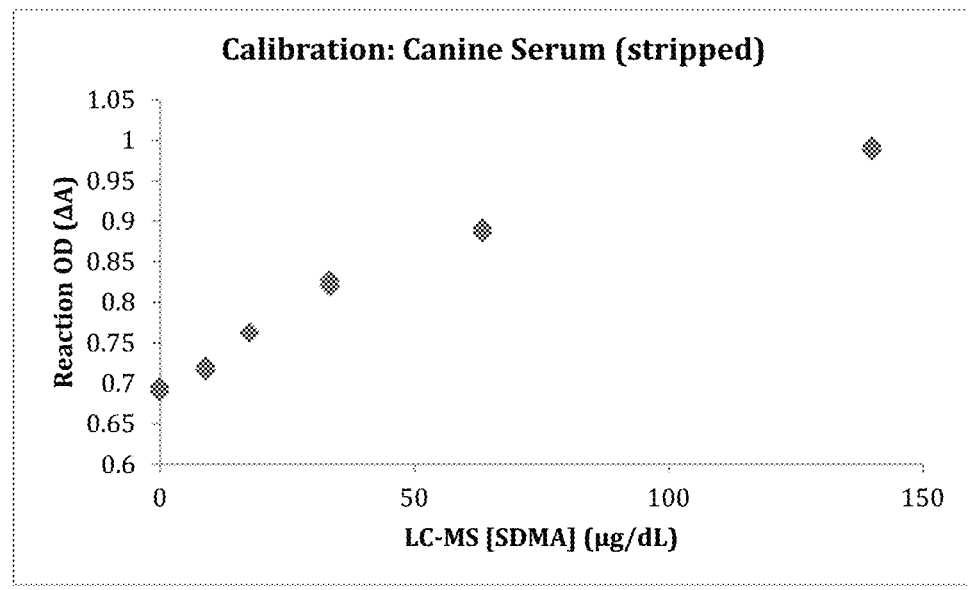
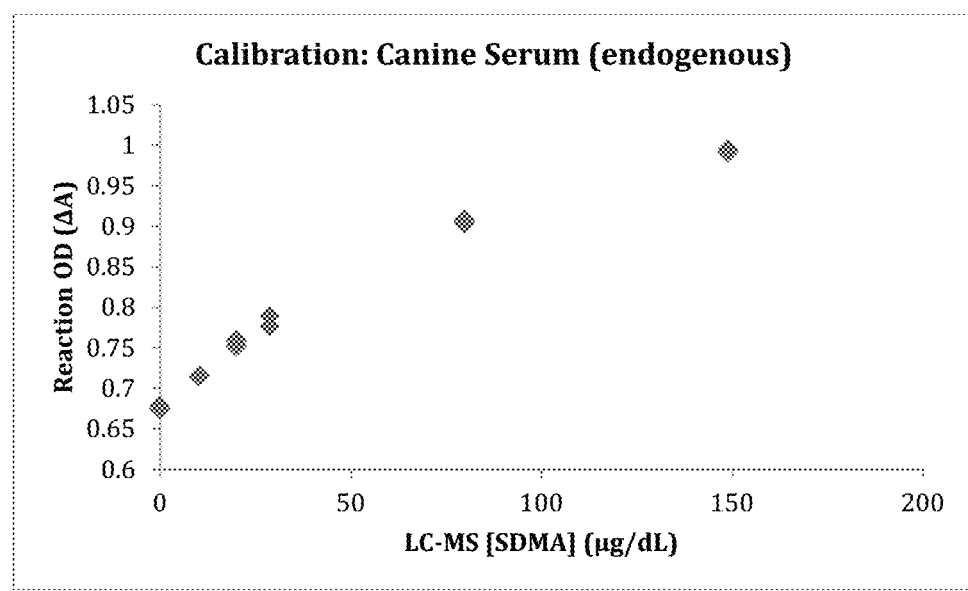

FIG 10
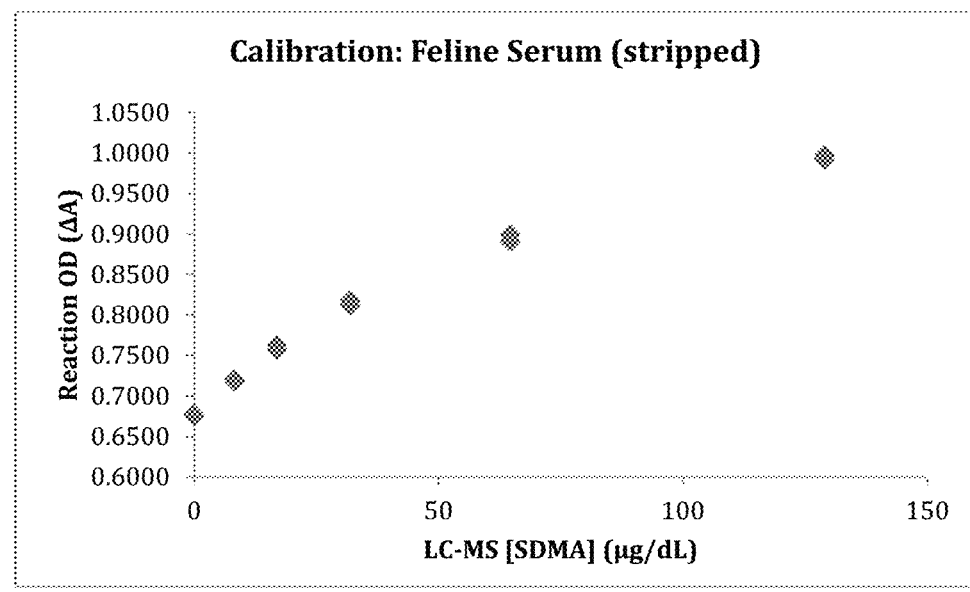
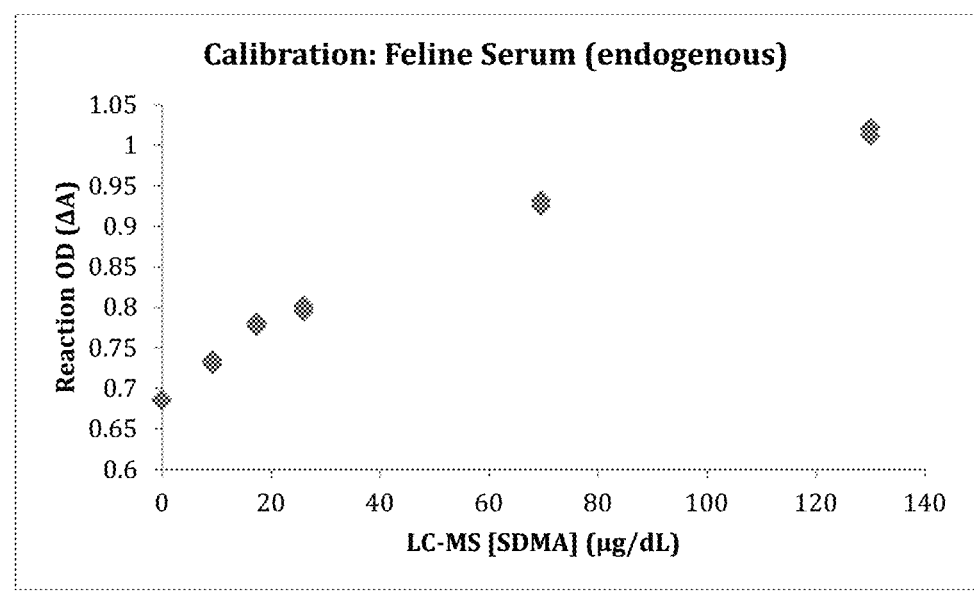

FIG. 11
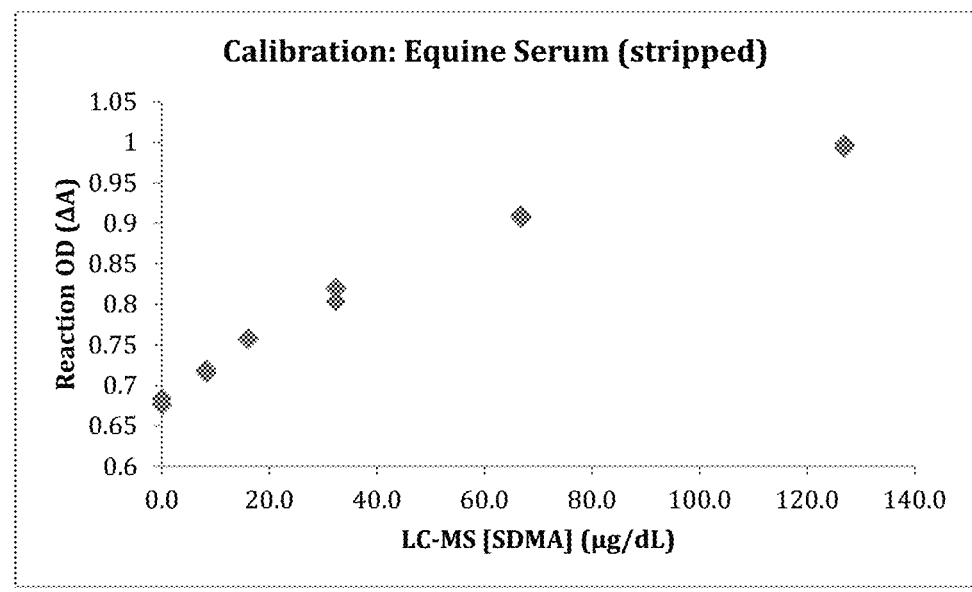
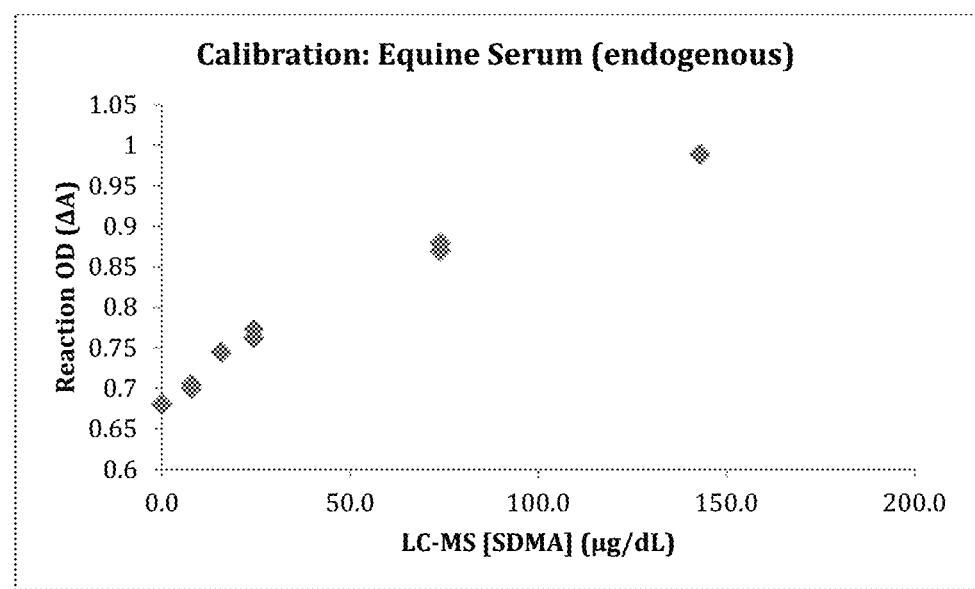

HOMOGENOUS IMMUNOASSAY WITH COMPENSATION FOR BACKGROUND SIGNAL

RELATED APPLICATION

This application claims the benefit of U.S. provisional patent application Ser. No. 62/118,832 filed Feb. 20, 2015, which is incorporated by reference herein in its entirety.

BACKGROUND

Field

The disclosure generally relates to the homogeneous immunoassays that allow for compensation of background signals inherent in samples and reagents. In particular embodiments, the disclosure is directed to the use of homogeneous immunoassays for the detection of the presence or amount of symmetrical dimethyl arginine (SDMA) in biological samples.

Background

Homogeneous immunoassays have been implements for the determination of a variety of analytes, most notably analytes for drugs of abuse. SDMA has been identified in biological samples as a marker for the assessment of, for example, renal function, cardiovascular function, and SLE. SDMA is typically present in biological samples in a relatively low concentration compared to analytes for drugs of abuse.

Accordingly, the inventors have identified a need in the art for more accurate and sensitive homogeneous immunoassays, in particular for analytes such as SDMA that have low concentration in biological samples.

SUMMARY

In one aspect, the disclosure is directed to a conjugates of symmetrical dimethyl arginine (SDMA), for example conjugates of SDMA and an enzyme. In one example of the disclosure, the conjugate is SDMA conjugated to glucose-6-phosphate dehydrogenase (G6PDH). In various embodiments, the SDMA and the enzyme are conjugated through a 5 to 15 atom linker. Similarly, the SDMA may be enzyme through a linker having a length of about 5-15 Angstroms. Example conjugates of the disclosure include the following:

In another aspect, the disclosure is directed to composition including conjugates of the disclosure and an antibody specific for free SDMA. In various embodiments, the antibody specific for free SDMA may have reactivity for asymmetrical dimethylarginine (ADMA) of less than 25% of its reactivity for free SDMA. Similarly, the antibody may have no or substantially no cross-reactivity with one or more compounds selected from the group consisting of asymmetrical dimethylarginine (ADMA), L-arginine, and N-methylarginine.

In a further aspect, the disclosure is directed to kits that include a conjugate of the disclosure and an antibody specific for SDMA.

In various aspects, the kits of the disclosure include reagents for conducting an assay on a sample containing an analyte. The kits may include the following components
  (a) first set of reagents for conducting a first assay, including:
    i. a first reagent including an anti-analyte antibody and a signal producing substrate for an enzyme, and
    ii. a second reagent including a conjugate of the analyte and the enzyme, and
  (b) a second set of reagents for conducting a second assay, including
    i. a third reagent including the substrate.

In the kits, the second set of reagents may further include a fourth reagent including at least one of a diluent and a buffer. The fourth reagent may also further include the conjugate or the enzyme. In addition, at least one of the reagents in the kits includes an inhibitor for an enzyme other than the enzyme of the conjugate. In an embodiment, the concentration of the conjugate in the first reagent is about 5 to about 150 times more than the concentration of the conjugate in the fourth reagent. The kits many also include a standard including a known amount of the analyte diluted in a sample solution that has been stripped of the analyte. For example, the sample solution that has been stripped of the analyte may be stripped serum, stripped plasma, or a pretreated sample. The first reagent and/or the second reagent may further includes an electron mediator and a dye, and the third reagent and/or the fourth reagent may further include the mediator and the dye, wherein the mediator accepts an electron from the substrate and transfers it to the dye.

Still further, the disclosure is directed to reaction mixtures that include the components of the kits of the disclosure and a sample suspected of including SDMA.

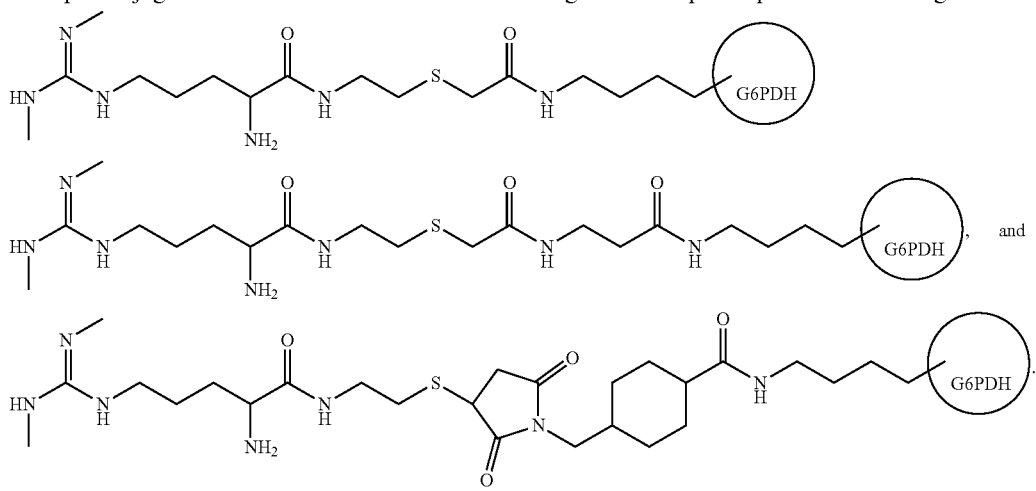

In yet another embodiment, the disclosure is directed to method for determining the presence or amount of free SDMA in a sample. The method includes contacting the sample with an anti-SDMA antibody specific for free SDMA, the conjugate of claim 1, and a substrate including Nicotinamide Adenine Dinucleotide (NAD), measuring the conversion of NAD to NADH, and determining the presence or amount of SDMA in the sample based upon the conversion of NAD to NADH.

In various embodiments of the methods of the disclosure, the measuring the conversion of NAD to NADH may include measuring the rate of conversion of NAD to NADH. For example, the determining the presence or amount of SDMA in the sample based upon the conversion of NAD to NADH may include comparing the rate of the conversion of NAD to NADH to a standard curve, or the measuring the conversion of NAD to NADH may include measuring an amount of conversion of NAD to NADH. The determining the presence or amount of SDMA in the sample based upon the conversion of NAD to NADH may also include comparing the amount of the conversion of NAD to NADH to a standard curve.

In another aspect of the methods of the disclosure, the methods include the following steps:
(a) conducting a sample first reaction sequence including:
  i. forming a sample first reaction mixture by contacting the sample with an anti-analyte antibody, a conjugate including the analyte and an enzyme, and a substrate that produces a signal when in contact with the enzyme, and
  ii. measuring signal from the sample first reaction mixture;
(b) conducting a sample second reaction sequence including,
  i. forming a sample second reaction mixture by contacting the sample with the substrate,
  ii. measuring signal from the sample second reaction mixture;
(c) subtracting an amount of signal from step (b) from an amount of signal from step (a) to provide a net signal,
(d) using the net signal to determine the amount of the analyte in the sample.

The methods of the disclosure may further include the following steps:
(a) conducting a calibrator first reaction sequence including:
  i. forming calibrator first reaction mixtures by individually contacting each calibrator of a set of calibrators including known amounts of the analyte with an anti-analyte antibody, a conjugate including the analyte and an enzyme, and a substrate that produces a signal when in contact with the enzyme, and
  ii. measuring signal from each of the calibrator first reaction mixtures;
(b) conducing a calibrator second reaction sequence including,
  i. forming calibrator second reaction mixtures by contacting each calibrator of the set of calibrators with the substrate, and
  ii. measuring signal from the calibrator second reaction mixtures;
(c) subtracting an amount of signal from step (a) from an amount of signal from step (b) to provide a net signal for each of the calibrators,
(d) using the net signal from two or more of the calibrators to generate a standard curve,
(e) determining the amount of the analyte in the sample by comparing the net signal from the sample to the standard curve.

In other embodiments of the method of the disclosure, the methods may include the following steps:
(a) conducting a sample first reaction sequence including:
  i. forming a sample first reaction mixture by contacting the sample with an anti-analyte antibody, a conjugate including the analyte and an enzyme, and a substrate that produces a signal when in contact with the enzyme, and
  ii. measuring signal from the sample first reaction mixture;
  iii. normalizing a reaction rate for the sample first reaction mixture by accounting for background associated with the sample first reaction mixture,
(b) conducting a sample second reaction sequence including,
  i. forming a sample second reaction mixture by contacting the sample with the substrate,
  ii. measuring signal from the sample second reaction mixture;
  iii. normalizing a reaction rate from the sample second sample reaction mixture by accounting for background associated with the sample second reaction mixture,
(c) subtracting the normalized rate of step (b)(iii) from the normalized rate of step (a)(iii) to provide a final reaction rate for the sample containing the analyte,
(d) using the final reaction rate to determine the amount of the analyte in the sample.

The methods of the disclosure may also include the following steps:
(a) conducting a calibrator first reaction sequence including:
  i. forming calibrator first reaction mixtures by individually contacting each calibrator of a set of calibrators including known amounts of the analyte with an anti-analyte antibody, a conjugate including the analyte and an enzyme, and a substrate that produces a signal when in contact with the enzyme, and
  ii. measuring signal from each of the calibrator first reaction mixtures;
  iii. normalizing a reaction rate from each of the calibrator first reaction mixtures by accounting for background associated with each of the calibrator first reaction mixtures,
(b) conducing a calibrator second reaction sequence including,
  i. forming calibrator second reaction mixtures by contacting each calibrator of the set of calibrators with the substrate,
  ii. measuring signal from the calibrator second reaction mixtures;
  iii. normalizing a reaction rate for each calibrator in the calibrator second reaction mixtures by accounting for background associated with the calibrator second reaction mixtures,
(c) subtracting the normalized rates of step (b)(iii) from the normalized rates of step (a)(iii) to provide a final reaction rate for each of the calibrators,
(d) generating a normalized standard curve based upon the final reaction rate for each of the calibrators,
(e) determining the amount of the analyte in the sample by comparing the normalized reaction rate for the sample to the normalized standard curve.

In various aspects of the methods of the disclosure, the sample and calibrator second reaction mixtures may include any one or more of a diluent, a buffer, and an anti-analyte antibody. Also, the accounting for background associated with the sample first reaction mixture and/or the calibrator first reaction mixture may include subtracting the background from each of a plurality of signal measurements associated with the determination of a reaction rate for each sample and/or calibrator first reaction mixtures. Similarly, the accounting for background associated with the sample and/or calibrator second reaction mixtures includes subtracting the background from each of a plurality of signal measurements associated with the determination of a reaction rate for the sample second reaction mixture and/or each calibrator second reaction mixture.

In the methods of the disclosure, the sample may be a biological sample, such as serum, plasma, urine or cerebral-spinal fluid.

In the methods of the disclosure, the calibrator may include the analyte diluted in plasma or serum, including for example a stripped serum or plasma. In another embodiment, the calibrator may be a pretreated sample.

In further aspects of the methods of the disclosure, sample and/or calibrator second reaction mixtures may further include the conjugate. For example, the conjugate in the sample or calibrator first reactions mixture may be present at about 5 to about 150 times more than the concentration of the conjugate in the sample or calibrator second reaction mixtures.

Still further, in other aspects of the methods of the disclosure, any of the reaction mixtures may include an inhibitor for an enzyme other than the enzyme of the conjugate. In addition, any of the reaction mixtures may further include an electron mediator and dye, wherein the mediator accepts an electron from the substrate and transfers it to the dye.

In yet another aspect, the disclosure is directed to a method for determining chronic kidney disease in an animal. The method includes determining the presence or amount of SDMA in a biological sample from an animal according to methods of the disclosure, and determining chronic kidney disease in the animal based upon the presence amount of SDMA in the sample.

BRIEF DESCRIPTION OF THE FIGURES

FIGS. 9, 10 and 11 show the results of an SDMA assay according to the disclosure using canine (FIG. 9), feline (FIG. 10), and equine (FIG. 11) stripped serum calibrators.

DESCRIPTION

Figure 1:
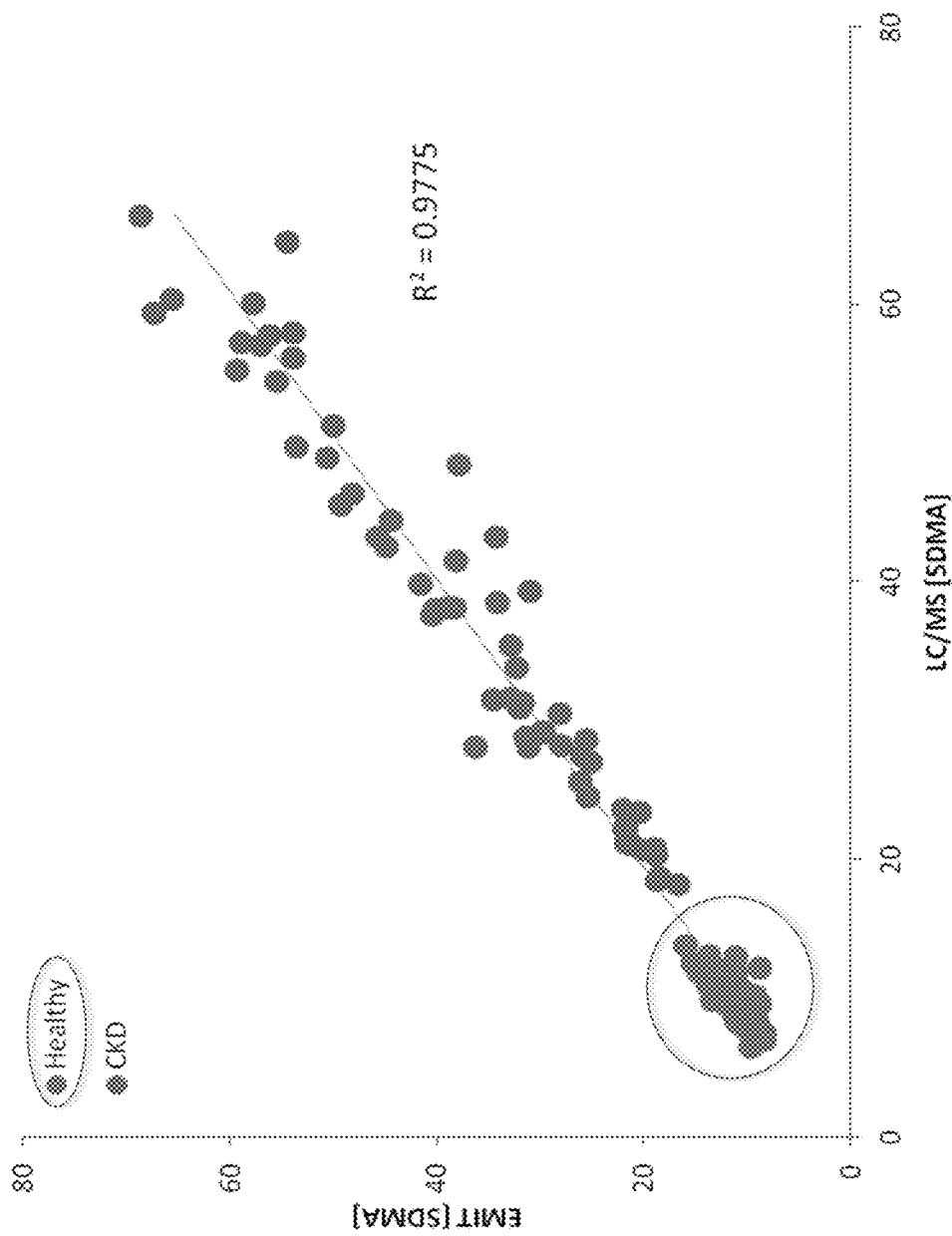
FIG. 1 shows the results of the assay of the disclosure on human serum samples from a normal population and patients suffering from Chronic Kidney Disease (CKD).

Before describing the present invention in detail, a number of terms will be defined. As used herein, the singular forms "a," "an", and "the" include plural referents unless the context clearly dictates otherwise.

SDMA is symmetrical dimethylarginine. The structure of SDMA is:

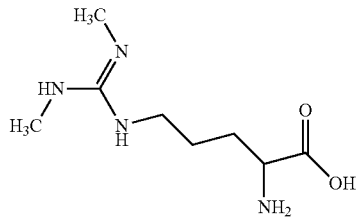

While one or more amino acid residues of SDMA can be present in a polypeptide, "free SDMA" refers to SDMA that is not part of a polypeptide chain, including salts of SDMA.

The term "analog," as used herein, generally refers to a modified form of the analyte which can compete with the analyte for a receptor, the modification providing a means to join the analyte to another moiety, such as a label or solid support. The analyte analog can bind to an antibody in a manner similar to the analyte.

The term "antibody," as used herein, generally refers to a glycoprotein produced by B lymphocyte cells in response to exposure to an antigen and binds specifically to that antigen. The term "antibody" is used in its broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, an "anti-SDMA antibody," "anti-SDMA antibody portion," or "anti-SDMA antibody fragment" and/or "anti-SDMA antibody variant" and the like include any protein or peptide containing molecule that includes at least a portion of an immunoglobulin molecule, such as, but not limited to, one complementarity determining region (CDR) of a heavy chain or light chain constant region, a framework region, or any portion thereof.

The term "antibody fragment," as used herein, refers to a portion of a full length antibody, generally the antigen binding or variable domain thereof. Specifically, for example, antibody fragments may include Fab, Fab', F(ab')$_2$, and Fv fragments; diabodies; linear antibodies; single-chain antibody molecules; and multispecific antibodies from antibody fragments.

The term "antigen," as used herein, generally refers to a substance that is capable, under appropriate conditions, of reacting with an antibody specific for the antigen.

The term "analyte," as used herein, generally refers to the substance, or set of substances in a sample that are detected and/or measured.

The term "biological sample," as used herein, generally refers to a sample of tissue or fluid from a human or animal including, but not limited to whole blood, plasma, serum, spinal fluid such as cerebral-spinal fluid; lymph fluid, abdominal fluid (ascites), the external sections of skin, respiratory, intestinal and genitourinary tracts, tears, saliva, urine, blood cells, tumors, organs, tissue, and sample of in vitro cell culture constituents.

The term "cross-reactivity," as used herein, generally refers to the ability of an individual antigen binding site of an antibody to react with more than one antigenic determinant or the ability of a population of antibody molecules to react with more than one antigen. In general, cross reactions arise because (i) the cross reacting antigen shares an epitope in common with the immunizing antigen or (ii) it has an epitope which is structurally similar to one on the immunizing antigen (multispecificity).

The term "label," as used herein, refers to a detectable compound or composition that can be conjugated directly or indirectly (e.g., via covalent or non-covalent means, alone or encapsulated) to an analyte analog, e.g., an SDMA analog. For instance, an enzymatic label may catalyze chemical alteration of a substrate compound or composition which is detectable. The enzymes employed in the current disclosure could be, but are not limited to: alkaline phosphatase (AP); glucose-6-phosphate dehydrogenase ("G6PDH"); Beta Galactosidase (B GAL); and horse radish peroxidase (HRP), malate dehydrogenase (MDH). Any recitations of an enzyme, such as "G6PDH" or "glucose-6-phosphate dehydrogenase" herein, also include variants, isoforms and mutants of the enzyme, for example G6PDH having the amino acid substitutions as described in U.S. Pat. No. 6,455,288, which is incorporated by reference herein in its entirety. The utilization of a label produces a signal that may be detected by means such as detection of electromagnetic radiation or direct visualization, and that can optionally be measured.

The term "monoclonal antibody," as used herein generally refers to an antibody obtained from a population of substantially homogeneous antibodies, i.e., the individual antibodies including the population are identical. Monoclonal antibodies are highly specific, being directed against a single antigenic site. In contrast to polyclonal antibody preparations, which typically include different antibodies directed against different epitopes, each monoclonal antibody is directed against a single epitope on the antigen. The modifier "monoclonal" merely refers to the character of the antibody and is not to be construed as requiring production of the antibody by any particular method. Specifically, for example, monoclonal antibodies may be made by hybridoma methodologies, or may be made by recombinant DNA methods, or may be isolated from phage antibody libraries using known techniques.

The term "polypeptide," as used herein, generally refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the disclosure, treated as a subclass of the polypeptides and polypeptide derivatives.

"Receptor" refers to any compound or composition capable of recognizing a particular spatial and polar organization of a molecule, e.g., epitopic or determinant site. Illustrative receptors include antibodies, Fab fragments, and the like.

"Binding specificity" or "specific binding" refers to the substantial recognition of a first molecule for a second molecule, for example an analyte, such as SDMA, and a polyclonal or monoclonal antibody, or an antibody fragment (e.g. a Fv, single chain Fv, Fab', or F(ab')2 fragment) specific for the analyte. For example, "specificity," as used herein, generally refers to the ability of an individual antibody combining site to react with only one antigenic determinant or the ability of a population of antibody molecules to react with only one antigen. In general, there is a high degree of specificity in analyte-antibody reactions. Antibodies can distinguish differences in (i) the primary structure of an analyte, (ii) isomeric forms of an analyte, and (iii) if applicable, secondary and tertiary structure of an analyte. Antibody-analyte reactions that exhibit high specificity exhibit low cross reactivity.

"Substantial binding" or "substantially bind" refers to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules and the time and temperature of an incubation. In another aspect, one molecule is substantially incapable of binding or recognizing another molecule in a cross-reactivity sense where the first molecule exhibits a reactivity for a second molecule that is less than 25%, for instance less than 20%, less than 15%, less than 10%, less than 5% or less than 1% of the reactivity exhibited toward a third molecule under a particular set of assay conditions. Specific binding can be tested using a number of widely known methods, e.g., an immunohistochemical assay, an enzyme-linked immunosorbent assay (ELISA), a radioimmunoassay (MA), or a western blot assay.

The term "salt," as used herein, means a salt formed between an acid and a basic functional group of a compound. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "salt" also refers to a salt formed between a compound having an acidic functional group, such as a carboxylic acid functional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-sub stituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris- (hydroxymethyl)methylamine, N, N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

Turning now to the disclosure, in general, the disclosure is directed the immunodetection of analytes in samples in a manner that addresses the background signal associated with sample and reagent components other than the analyte. For instance, the sample components other than the analyte may react with each other or with components of the reagents for the assays. Such reactions can lead to interference with the accuracy of the detection method. Biological samples are notorious for including many components that can create background noise in assays.

Samples may be analyzed using a modified assay based upon the EMIT® (Enzyme Multiplied Immunoassay Technique) homogeneous immunoassay system. In a traditional EMIT® assay, a sample containing the analyte is contacted with an anti-analyte antibody, a conjugate of the analyte and an enzyme, and a substrate that produces a signal when in contact with the enzyme. Binding of the antibody to the conjugate inhibits or reduces enzyme activity. When analyte is present in the sample, the sample analyte competes with the conjugated analyte for binding to the antibody, which results in the generation of more signal from the enzyme/substrate. When no analyte is present, more binding can occur between antibody and conjugate to limit or prevent signal generation. Therefore, more signal is generated when more analyte is present. Kinetic assays can use the rate of signal generation as an indicator of the presence or amount of analyte in a sample In one aspect of the disclosure, the traditional EMIT® assay format is conducted in a first reaction sequence for both the analyte and the calibrators. For convenience, this first reaction sequence may be identified herein as the "Color Assay." Then, in the modified assay of the disclosure, a second and separate assay is conducted in a second reaction sequence for the sample and calibrators. For convenience, the second reaction sequence may be identified herein as the "Blank Assay." The reagents of the Blank Assay do not contain anti-analyte antibody and typically does not contain conjugate. Therefore, the Blank Assay provides a sample-dependent background signal.

In various aspects, disclosure is directed to the use of the signal in two example methods for determining the concentration of an analyte. For convenience the example methods are referred to herein as the "Rate" method and the "Fixed" method. In both methods, the difference between an amount of signal or signals in the Color and Blank assays is used. In one aspect, signal is measured as absorbance at a wavelength specific for an enzyme/substrate system as is well known in the art. For instance, measurement of absorbance at 340 nm for a G6PDH/NAD enzyme/substrate system will provide a value for the relative amount of conversion of NAD to NADH in the presence of G6PDH. The value can be used to provide a net signal (for the Fixed method) or a reaction rate (for the Rate method) reflecting the conversion of the substrate by the enzyme. As an alternative, the enzyme substrate reaction can be used in conjunction with an electron carrier that mediates electron transfer between the substrate and various electron acceptors (e.g., a dye) that will allow for measurement of the reaction rate at a different wavelength than that of the substrate.

In the Fixed method, a net signal is calculated. In one embodiment, the net signal is based upon the difference in signal (e.g., absorbance) between the Color and Blank assays at a predetermined end point, which may or may not be the completion of the reaction by exhaustion of all substrate. The amount of difference in signal measured at the end point of the Blank and Color assays may be used to provide a net signal (e.g., Net Signal=[amount of Color signal]-[amount of Blank signal]). Alternatively, the difference in the amount of signal between a predetermined starting point T1 (which may be at the completion of the combination all reagents or another predetermined time thereafter) and the predetermined end point (T2) can be determined for both the Color and Blank assays can be determined. The difference in the amount of signals from these determinations can then be used to determine the net signal (e.g., Net Signal=([T2 Color]-T1 Color])-([T2 Blank]-[T1 Blank])). The net signal can be compared to a calibration curve to determine the amount of analyte in the sample.

When the net single is calculated based upon a single measurement from each of the Color and Blank assays, the measurements may be taken after the reagents have had a sufficient to time to react. For example, the single measurement in each assay may be taken at about 30 second to about 10 minutes following the combination of all of the reagents. More particularly, the single measurement may be taken at one of 30, 60, 90, 120, 150, 180, 210, 240, 270, 300, 330, 360, 390, 420, 450, 480, 510, 540, 570 and 600 seconds following the combination of all of the reagents. When two signals are measured in each of the Blank and Color assays, the first measurement (T1) is taken after about 15 second to two minutes from the beginning of assay (combination of sample and all reagents). This time can be adjusted based upon the concentration of reagents and the expected concentration of the sample. In particular, T1 may be 15, 30, 45, 60, 75, 90, 105 or 120 seconds following the combination of all the reagents. The second measurement (T2) can be taken from 15 seconds to several minutes following T1. For example, T2 may be for example, 15 seconds, 18 seconds, 30 seconds, 45 second, or 1, 2, 3, 4, or 5 minutes, after the first measurement (T1).

In the Rate method, the signal from the Blank Assay is subtracted from the signal of the Color assay at defined intervals to provide a reaction rate. The reaction rates of calibrators are used to provide a calibration curve that can be used to determine the amount of analyte in the sample by comparing the curve to the reaction rate of the assay on the sample to the calibration curve.

In the Rate method, the reaction rate can be determined by measuring signal (e.g. absorbance) at a plurality of time points during the enzyme mediated reaction. Determination of the time and interval of signal measurement are within the skill in the art taking into consideration the concentration of the reagents and the temperature of the assay. For instances, a rate can be determined by measuring absorbance beginning about 2-10 minutes after the combination of sample (or calibrator) and all reagents at room temperature and measured every 5-60 seconds for an additional 1-15 minutes. Reaction rate can be expressed as the change in absorbance over time. For example, absorbance can be measured starting at about 1, 2, 3, 4, 5, 6, 7, 8, 9, or 10 minutes after combining the sample (or calibrator) and all the reagents. Absorbance is typically measured at intervals of 5, 10, 15, 20, 25, 30, 35, 40, 45, 50, 55 or 60 seconds for about 2, 3, 4, 5, 6, 7, 8, 9, 10, 11, 12, 13, 14 or 15 minutes. Each of these times can be extended or shortened, depending on reaction conditions, analyte, and reagents.

In either the Fixed or Rate methods, background from sample first reaction mixture can be accounted for in calculation of the net signal or reaction rate to provide a normalized signal. In one embodiment, the background absorbance is measured from a calibrator matrix used in place of the sample. The absorbance of the calibrator matrix is measured initially upon the combination of all of the reagents with the matrix, or at a finite time thereafter. The calibrator matrix may be a calibrator or control mixture lacking any analyte. For example, a calibrator matrix lacking analyte may be the sample that has been stripped of the analyte by dialysis or by another pretreatment process as further described herein. In one embodiment, stripped or endogenous species specific or non-specific serum, plasma, or other biological fluid may be used as the calibrator matrix. In other embodiments as further described herein, the calibrator matrix may be water or a diluent containing protein and/or other compositions (e.g., BSA in PBS). The calibrator matrix is used in place of the sample in both the Color Assay and the Blank Assay to provide a background signal for both Assays.

If the background has been determined, the background is then subtracted from the net signal in the Fixed method (or measurements at T1 and T2) or from each measurement used to determine the sample reaction rate in the Rate method. As an example, in the Rate method, the absorbance of the calibrator matrix (with reagents) is subtracted from each absorbance measurement that is used to determine the reaction rate for the sample (i.e., change in absorbance over time). In another aspect, a background rate is determined in a manner similar to the sample reaction rate. The background rate is then subtracted from sample reaction rate to provide a normalized reaction rate for the first sample reaction mixture.

Accordingly, the disclosure is directed to methods for conducting an assay for an analyte. The method includes conducting the Color Assay on the sample (sample first reaction sequence) by forming a sample first reaction mixture including the sample, an anti-analyte antibody, a conjugate including the analyte and an enzyme, and a substrate that produces a signal when in contact with the enzyme. Typically, the sample first reaction mixture is formed by first contacting the sample with the antibody and the substrate, and then in a second step adding the conjugate. However, the sample may be first combined with the antibody and the conjugate, and the substrate added in a second step. In one aspect, the enzyme and conjugate are kept separate until the reaction sequence is ready to begin. "Contacting" as used here is used in its broadest aspect to refer to combining reagents in any order unless otherwise specified herein. Once the sample first reaction mixture has been formed, an amount of signal may be measured from the mixture immediately or at one or more predetermined times thereafter for use in the Fixed or Rate methods of the disclosure.

In the modified Fixed and Rate methods of the disclosure, a separate assay sequence (sample second reaction sequence or "Blank Assay") is conducted in a manner similar to the sample first reaction sequence. However, the reagents of the sample second reaction sequence do not contain anti-analyte antibody. Typically, the reagents of the Blank Assay do not contain conjugate, but described herein are embodiments where a small amount of conjugate or enzyme is added. In particular, a sample second reaction mixture is formed by contacting the sample with the substrate and, in some instances, the conjugate but no anti-analyte antibody. Signal is measured from the sample second reaction mixture. The net signal or reaction rate using the background from the calibrator matrix is determined in a manner identical to the sample first reaction sequence to provide a normalized net signal or a normalized reaction rate for the sample second reaction sequence.

In the Rate method, to provide a final reaction rate for the sample, the normalized rate of sample second reaction sequence is subtracted from the normalized reaction rate of the sample first reaction sequence. The final reaction rate can be used to determine the presence or amount of the analyte in the sample. Typically, this is done by comparing the final reaction rate for the sample to a standard curve, which can be prepared according to methods known in the art.

The Color and Blank assays for the calibrators can be conducted in manner similar to the Color and Blank assays for the sample. Accordingly, a series of calibrator first reaction sequences (Color Assays) is conducted by forming calibrator first reaction mixtures by individually contacting each calibrator of a set of calibrators including known amounts of the analyte with an anti-analyte antibody, a conjugate including the analyte and an enzyme, and a substrate that produces a signal when in contact with the enzyme. Signal is measured from each of the calibrator first reaction mixtures and a normalized net signal (Fixed method) or normalized reaction rate (Rate method) for each of the calibrator first reaction mixtures is generated by accounting for background associated with each of the calibrator first reaction mixtures in the manner described above for the sample first reaction mixtures. One of the calibrators may be the calibrator matrix (which contains no analyte) that is used to determine background.

In a separate reaction series (Blank Assays), calibrator second reaction sequence are performed by forming calibrator second reaction mixtures by contacting each calibrator of the set of calibrators with the substrate in the absence of anti-analyte antibody and, typically, conjugate. In some instances, the conjugate may also be present, usually in a small amount as described further herein. Signal is measured for each of the calibrator second reaction mixtures, and the net signal or reaction rate for each mixture is normalized by accounting for background associated with the calibrator second reaction mixtures in the manner described above.

Accordingly, in accounting for background signal in the fixed method, the normalized net signal from the Blank assay is subtracted from a normalized net signal from the Color assay. In the Rate method, a final reaction rate for each of the calibrators is determined by subtracting the normalized rate from the calibrators in the calibrator second reaction sequences from the normalized rate for each of the calibrators in the calibrator first reaction sequences. A normalized standard curve based upon the final reaction rate for each of the calibrators can then be prepared and used to determine the amount of the analyte in the sample by comparing the normalized reaction rate for the sample to the normalized standard curve.

In one embodiment, the reagents associated with the Color Assay and Blank Assays are shown in Table 1. The reagents are combined in the appropriate diluent and/or buffers. As shown in Table 1, Blank Assay reagent 2 (R2) does not contain the conjugate, although it may be present as further described herein to ensure that the reaction has the proper volume of buffer. In some aspects, Blank Assay R1 may have extra volume in the event that Blank Assay R2 is not used. In one embodiment, the reagents for the Color Assay are identical to the reagents for the Blank Assay except for the presence or absence of the antibody and conjugate. When R2 does not contain any conjugate in the Blank Assay, it still contains the diluent, buffer and other components of R2 for the Color Assay.

TABLE 1

| Reagent Components | Color Assay R1 | Color Assay R2 | Blank Assay R1 | Blank Assay R2 |
|---|---|---|---|---|
| Anti-Analyte Antibody | X | | | |
| Enzyme substrate | X | | X | |
| Enzyme analyte conjugate | | X | | |

In some embodiments, Blank Assay R1 may also contain the anti-analyte antibody.

Calibrators and test samples in the Color Assay can commonly be expected to produce an increase in absorbance due to the analyte-enzyme conjugate that is added to the reaction mixture. Many samples also produce a positive reaction when tested in the Blank Assay because endogenous enzymes reactive with endogenous substrates or with the substrate of R1 will produce an increase in absorbance even without conjugate present. Often, however, samples and calibrators are diluted to the extent that a usually small background signal is weakened further such that the reaction mixtures will produce little to no change in absorbance when tested in the Blank Assay. Because the change of absorbance may fall below the sensitivity range of a detector, it can lead to calibration curve failure on automated analyzers.

In order to avoid this problem, enzyme or analyte-enzyme conjugate can be added to the Blank Assays to ensuring that a small positive change in absorbance is produced (regardless of the calibrator or sample behavior). Accordingly, Table 2 shows the reagents present in this embodiment.

TABLE 2

| Reagent Components | Color Assay R1 | Color Assay R2 | Blank Assay R1 | Blank Assay R2 |
|---|---|---|---|---|
| Anti-Analyte Antibody | X | | | |
| Enzyme substrate | X | | X | |
| Enzyme analyte conjugate | | X | | X (conjugate or enzyme) |

The concentration of enzyme or conjugate in R2 is typically kept low to prevent unnecessary noise in the assay for the calibrator matrix. For example, when the enzyme is G6PDH, about 1-15 ng/mL of the enzyme (either conjugated or unconjugated) can be added to the Blank Assay. In particular, about 1, 2, 3, 4, 5, 6, 7, 8, 9, 10, 11, 12, 13, 14 or 15 ng/ml may be added. The amount of the conjugate in R2 depends on the size of the analyte, as larger analytes will require greater quantities of conjugate to provide the same amount of enzyme. In one embodiment, the concentration of the enzyme (either alone or conjugated) in R2 for the Color Assay is about 10 to about 150 times more than the concentration of the enzyme in R2 for the Blank Assay. In various embodiments, the concentration of the conjugate in the Color Assay is 10, 20, 30, 40, 50, 60, 70, 80, 90, 100, 110, 120, 130, 140 and 150 times more than the concentration of the enzyme in the reagents for the Blank Assay. When conjugated, the activity of the enzyme is typically less than that of the unconjugated enzyme. For instance, the activity of the conjugated enzyme varies widely from the activity of the unconjugated enzyme, for example the activity of the conjugate enzyme is 10%, 20%, 30%, 40%, 50%, 60%, 70%, 80% or 90% of the unconjugated enzyme. Therefore, when unconjugated enzyme is used in the R2 for the Blank assay, it can be used in a small amount than if it were conjugate and still provide the same activity as the conjugated enzyme.

Substrate, or substrates when the enzyme has more than one substrate, may be present in the reagents in excess.

In some aspects, the assay reagents can include stabilizers of assay reagents. For example, when the signal producing enzyme is glucose-6-phosphate dehydrogenase (G6PDH), glucose-6-phosphate (G6P), or NAD, can be added to conjugate containing reagent to stabilize the enzyme-analyte conjugate.

Serum contains several enzymes that can contribute to background. Therefore, the addition of specific enzyme inhibitors to the reagent diluents can further improve assay accuracy. The inhibitors help eliminate a portion of the interfering noise in the color and blank assays. Accordingly, in various aspects, the reaction components can include inhibitors of endogenous sample enzymes. For example, sodium oxamate is a known inhibitor of lactate dehydrogenase (LDH), which is an enzyme of NAD and/or NADP. Sodium oxamate prevents background signal associated with endogenous sample LDH by preventing LDH from turning over NAD in the sample or that may be part of the enzyme-substrate system associated with the assay (e.g., G6PDH/NAD). Over thirty serum enzyme and enzyme inhibitor combinations are known and inhibitors are available for many of them.

In one aspect, the calibrators include known quantities of the analyte (or none for the calibrator matrix) in dionized water or saline to provide the calibration matrix that is used in place of the sample. In other aspects, stripped serum is used instead of water or saline. The dialyzed serum is natural, species specific or non-specific serum or plasma that has been stripped the analyte in, for example, a dialysis process. Numerous other sample pretreatment processes are known to remove or inactivate the analyte. In each of these embodiments, the solutions are spiked with known quantities of the analyte to provide a series of calibrators over the expected range of concentration of the analyte in the sample. In yet another embodiment, the calibration solutions is a protein based solution such as 1-7% BSA in PBS. In this embodiment, it may be required to calibrate the BSA calibrators to stripped and spiked serum calibrators.

Typically, because the Blank Assay is intended to compensate for endogenous proteins, enzymes or other large molecule components that contribute to background signal, water or saline are more suited for non-biological samples, although sufficient specificity may be obtained with the use of water or saline as a calibrator solution for biological samples in many instances. Also, the use of water or saline buffer for the calibrator matrix in automated analyzers may have the tendency to create an error message for the calibrator matrix because the reaction rate associated with the use of buffer can result in significantly increased reaction rates compared to serum. In this situation, the subtraction of the absorbance value of the calibration matrix could result in a negative rate. While these rates can be normalized against serum-based calibrator matrices, automated analyzers will typically create an error message in this situation.

According to one embodiment of the disclosure, the analyte is SDMA and the enzyme-conjugate system is G6PDH/NAD. In this embodiment, an analog of SDMA is conjugated to G6PDH and used as the conjugate in the Color and Blanks Assays in order to determine the presence or amount of SDMA in serum or plasma samples from animals such as humans, cats and dogs. In one aspect of this embodiment, calibrators are prepared by combining known amounts of SDMA with in the calibrator matrix (stripped serum or plasma). Color and Blank assays are conducted as described above using the following reagents in exemplary amounts as described in Table 3:

TABLE 3

| Reagent Components | Color Assay R1 | Color Assay R2 | Blank Assay R1 | Blank Assay R2 |
|---|---|---|---|---|
| Anti-SDMA Antibody (µg/mL) | 4-10 | 0 | 0 | 0 |
| G6P (mM) | 8-75 | 1-5 | 8-75 | 2 |
| NAD (mM) | 8-75 | 0 | 8-75 (XS) | 0 |
| SDMA-G6PDH (µg/mL) | 0 | 0.25-0.75 | 0 | 5-30 (ng/mL) |

In particular the anti-SDMA antibody can have a concentration in R1 of the Color Assay from about 4 to about 10 µg/mL, for instance, about 4, 5, 6, 7, 8, 9 or 10 µg/mL. In R1 of the Color Assay or the Blank Assay, the G6P and NAD may have a concentration of about 8-75 mM, more particularly about 10-65 mM, or about 20-55 mM, and more particular about 8, 10, 15, 20, 25, 30, 35, 40, 45 50, 55, 60, 65, 70 mM. In R2 of the Color Assay, the SDMA-G6PHD conjugate may have a concentration of about 0.25 to about 0.75 µg/mL, more particularly about 0.25, 0.30, 0.35, 0.40, 0.45, 0.50, 0.55, 0.65, 0.70 or 0.75 µg/mL. In R2 of the Blank Assay, the concentration of the conjugate may be about 5-30 ng/mL, more particularly about 5, 10, 15, 20, 25 or 30 ng/mL.

G6P is present in the R2 reagents to stabilize the enzyme. Alternatively, NAD could be used. The stabilizing substrate is optional.

Reagents may be combined with the sample and calibrators at the following volumes for the Color and Blank Assays, although volumes may be adjusted to accommodate different analytes and reaction conditions:
Sample: 5-20 µL
R1: 20-60 µL
R2: 20-150 µL
In one particular embodiment, the reaction mixture contains 10 µl of sample, 40 µl of R1 and 125 µL of R2.

Using the above reagents in the Color and Blank assays, a calibration curve can be prepared and used to determine the presence or amount of SDMA in serum or plasma samples. FIG. 1 shows the results using the Rate method for the determination of SDMA in normal and chronic kidney disease human serum samples with a Beckman AU680® clinical chemistry analyzer. Results show accurate determination of SDMA concentration when compared to gold-standard LC-MS values. Human serum (unstripped) was used as the calibrator matrix. Accordingly, the disclosure is directed to a method of determining chronic kidney disease in animals, including humans, and, for example, domestic, farm, and zoo animals. The method includes determining SDMA concentration in a biological sample from an animal subject according to a method of the disclosure and comparing concentration to a standard curve or other model that the amount of SDMA in samples from the same species as the subject in healthy subjects and subject suffering from chronic kidney disease.

In one embodiment, disclosure is directed to a kit containing reagents for determining the presence or amount of analytes in samples. For example, the kit can include a first set of reagents for conducting the Color Assay, such as a first reagent including an anti-analyte antibody and a signal producing substrate for an enzyme, and a second reagent including a conjugate of the analyte and the enzyme. The kit may also include a second set of reagents that includes a third reagent containing the substrate. The second set of reagents may also include a fourth reagent containing the buffer/diluent, and optionally the conjugate. The purpose of the fourth reagent containing only buffer/diluent is to ensure that the reaction associated with the second set of reagents is conducted at the proper volume. When the second set of reagents does not include the fourth reagent, the volume of the third reagent should be adjusted accordingly. In addition, either the third or fourth reagent may contain the anti-analyte antibody.

The concentrations and amounts of the components in each reagent can be as described above for R1 and R2 in each of the Color and Blank Assays. For instance, the concentration of the conjugate in the first reagent is about 5 to about 150 times more than the concentration of the conjugate in the fourth reagent. In one aspect, at least one of the reagents in the kit includes an inhibitor for an enzyme other than the enzyme of the conjugate. The kit may also include a standard or set of standards (calibrators) that include a known amount of the analyte diluted an appropriate diluent, such as water, saline, or stripped or processed serum or plasma (e.g., a pretreated sample).

When the analyte is SDMA, an exemplary kit includes in the first reagent an anti-SDMA antibody (polyclonal or monoclonal) and substrate(s) such as NAD and G6P. The second reagent includes a conjugate of an SDMA analog and G6PDH as a stabilizer for the enzyme. The third reagent includes the SDMA-G6PDH conjugate and, optionally a fourth reagent. The fourth reagent may contain only diluent or buffer, or it may contain the conjugate.

In addition to kits, the disclosure is directed to a reaction mixture that includes reagents from the kits and a sample suspected of containing SDMA. For instance, the reaction mixture may include the sample or calibrator, the anti-SDMA antibody, the SDMA-G6PDH conjugate, NAD, and G6P.

In each of the kits, methods and reaction mixtures of the disclosure, a number of enzyme/substrates systems can be used in place of G6PDH/NAD. As another example, malate dehydrogenase is an enzyme catalyzes the oxidation of malate to oxaloacetate using the reduction of $NAD^+$ to NADH similar to G6PDH. In addition, many enzyme mutants are known which enhance the signal or stability of the enzymes. See, e.g., U.S. Pat. No. 6,455,288.

Analyte-enzyme conjugates can be prepared by a variety of known methods. Selection of the methods and the reagents employed can provide linkers of various lengths between the analyte and enzyme. Linker length can have an effect on the ability of the antibody to inhibit enzyme activity and to therefore affect assay sensitivity. Typically, linkers of about 5-15 atoms, or 2-20 Angstroms may be used. The conjugation of enzymes to analytes is within the skill in the art for many analytes that can be detected according to the disclosure.

Figure 2:
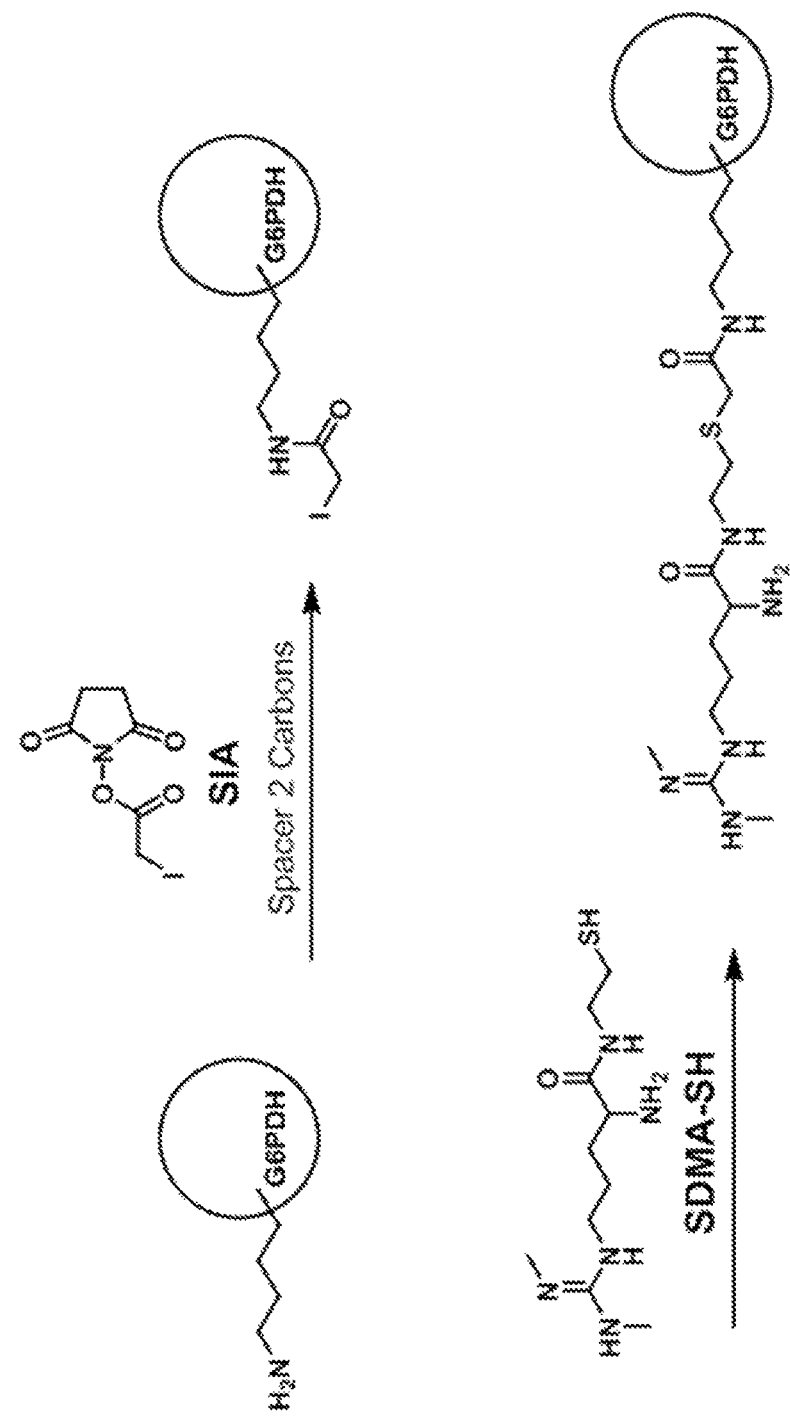
FIG. 2 shows a schematic representation of a procedure for conjugating SDMA to G6PDH using SIA to activate the G6PDH.

For instance, FIG. 2 shows the conjugation of SDMA analog of Formula 1 (below) to glucose-6-phosphate dehydrogenase (G6PDH). The G6PDH is activated with succinimidyl iodoacetate (SIA) prior to conjugation. The activation with SIA results in a five atom linker between SDMA and the enzyme (—C—C—S—C—C(O)—), which does not include the non-native nitrogen on the SDMA which results from replacement of oxygen with nitrogen during the derivitization of SDMA.

Figure 3:
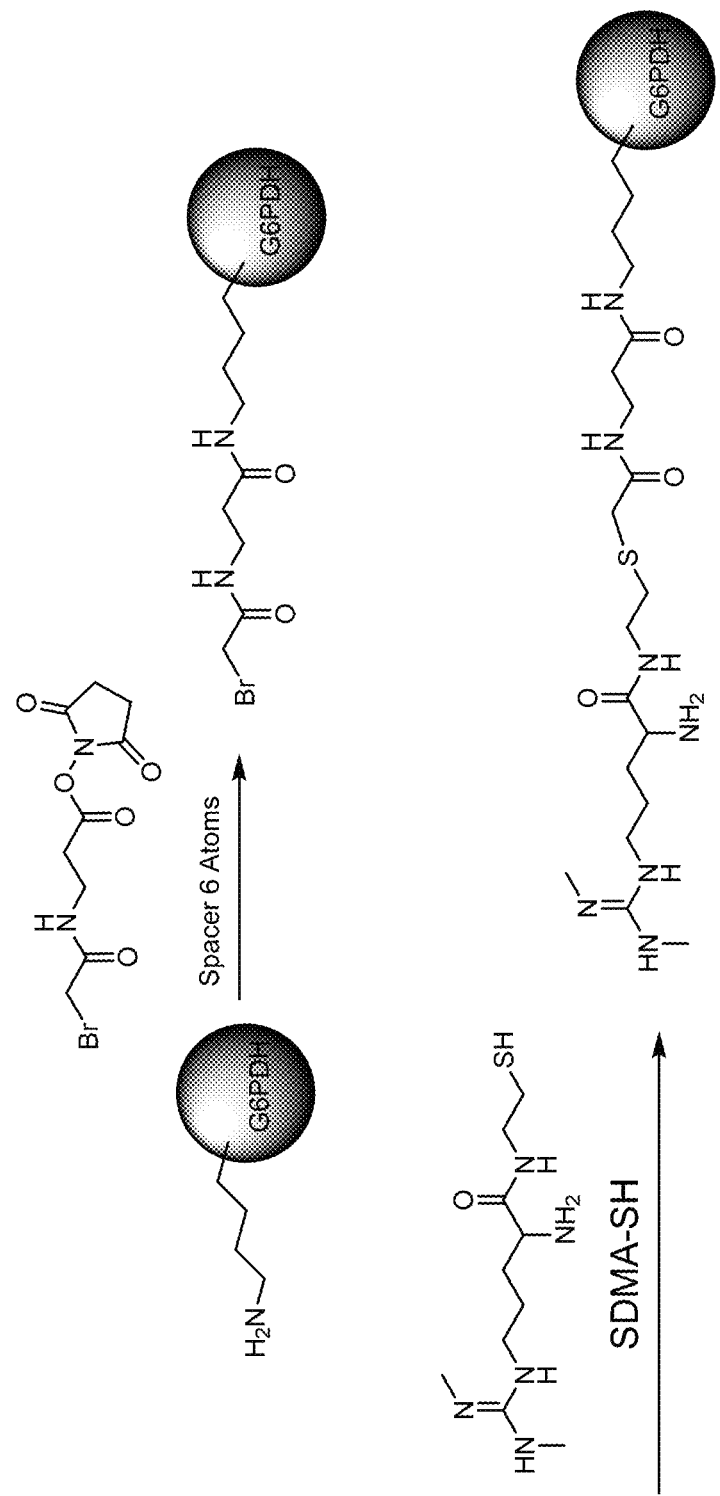
FIG. 3 shows a schematic representation of a procedure for conjugating SDMA to G6PDH using SBAP to activate the G6PDH.

FIG. 3 shows conjugation of the SDMA analog of Formula 1 to G6PDH using Succinimidyl 3-(bromoacetamido) propionate (SBAP) which results in a nine atom linker (not counting the non-native nitrogen) (—C—C—S—C—C (O)—C—N—C—C(O)—).

Figure 4:
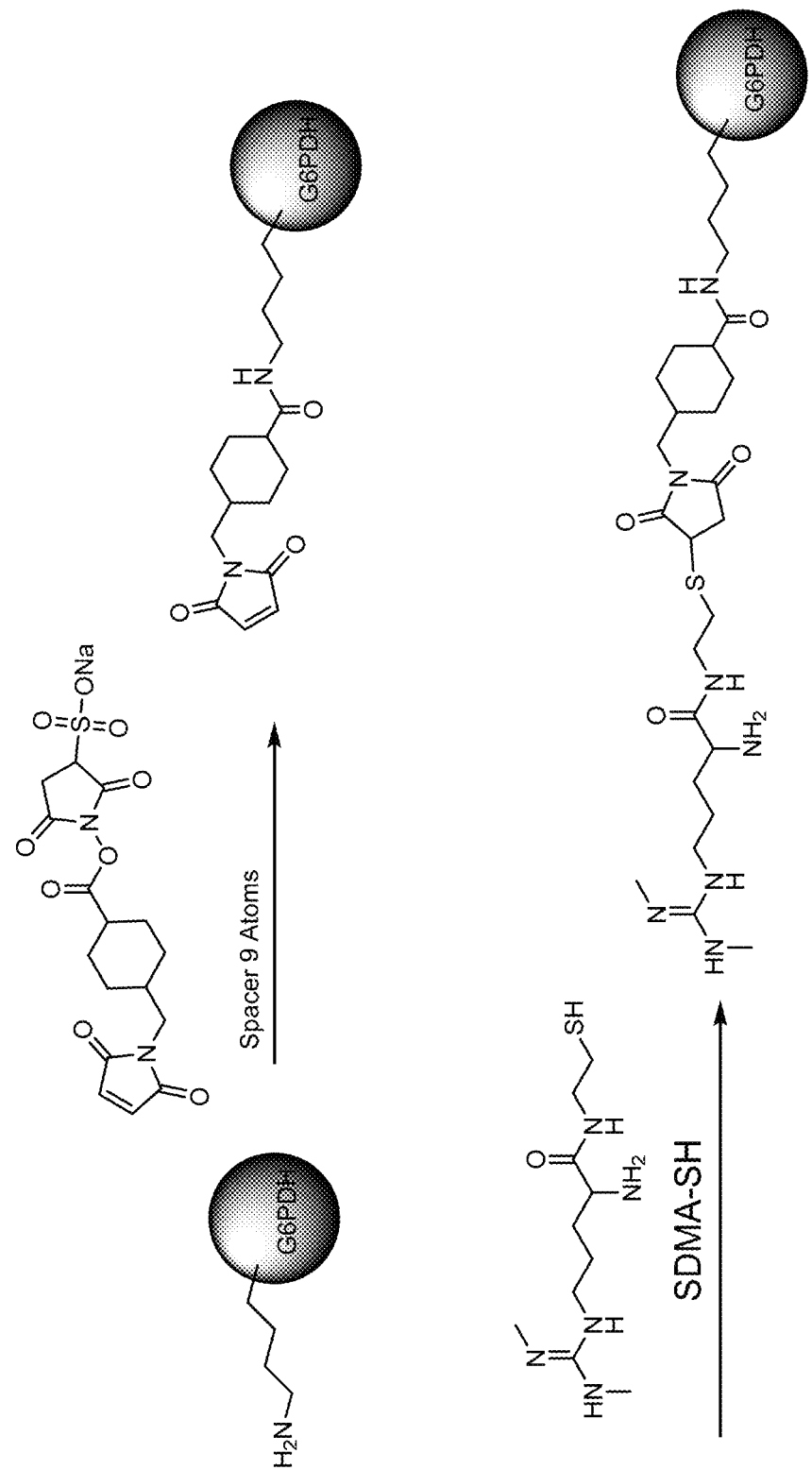
FIG. 4 shows a schematic representation of a procedure for conjugating SDMA to G6PDH using SMCC to activate the G6PDH.

FIG. 4 shows conjugation of the SDMA analog of Formula 1 to G6PDH using sulfosuccinimidyl-4-(N-maleimidomethyl)cyclohexane-1-carboxylate (SMCC) which results in a twelve atom linker.

Linker length can be adjusted by modifying G6PDH with other reagents or using other SDMA analogs in the conjugation reaction to provide linker lengths of, for example, about 5 to about 15 atoms, in particular about 5, 6, 7, 8, 9, 10, 11, 12, 13, 14 or 15 atoms. Accordingly, the disclosure is directed to a conjugate of SDMA and an enzyme through a linker of 5-15 atoms, which include only those atom in directly in the chain of the linker through the shortest route excluding any atoms of side chains, substituents, or rings in the linker molecule that are not part of the shortest route between the SDMA and enzyme.

Linker lengths can range from about 2 Angstroms to about 20 Angstroms, in particular about 5 to about 15 Angstroms, more particularly about 6-10 Angstroms.

In one embodiment, SDMA is conjugated to G6PDH in the presence of G6PDH substrates glucose-6-phosphate (G6P) and/or nicotinamide adenine dinucleotide (NADH). Optimal conjugate-enzyme activity and inhibition of that activity by the antibody can be obtained by adjusting the ratios of enzyme, substrates and SDMA.

Several analogs of SDMA that are appropriate for conjugation to G6PDH are described in U.S. Pat. No. 8,481,690, which is incorporated by reference herein in its entirety. Depending on the desired length of the linker between the SDMA and the G6PDH, one of the following analogs can be used:

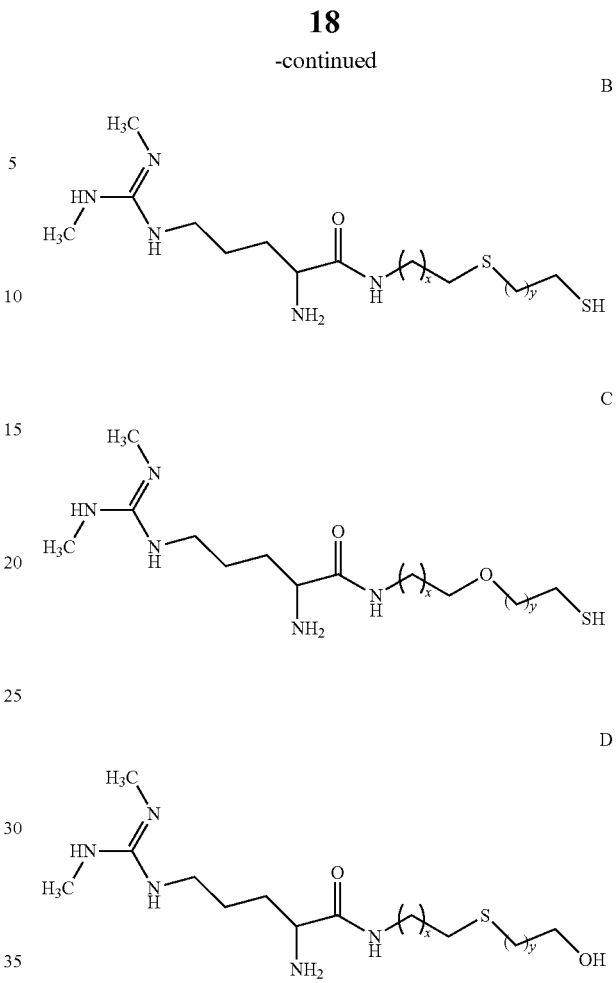

wherein x and y are integers ranging from 1 to 5.

Formulas A, B and C provide an available thiol that can react with a conjugation target that includes an appropriate "thiol-reactive site," i.e., a site that will react with a thiol group. For example, maleimides, alkyl and aryl halides, and alpha-haloacyls are illustrative thiol-reactive sites that can react with thiols to form thio-ethers. Similarly, pyridyl disulfides can react with thiols to form mixed disulfides. G6PDH activated with SIA, SBAP, or SMCC provide an appropriate thiol reactive site. When X=1, the conjugation of Formula A with SIA-activated G6PDH provides a five atom linker between the SDMA and G6PDH. Conjugation of Formula A (X=1) with SMCC results in a twelve atom linker. Other linker lengths can be obtain by varying X.

In one particular embodiment when X=1, the SDMA analog has the following formula (Formula 1):

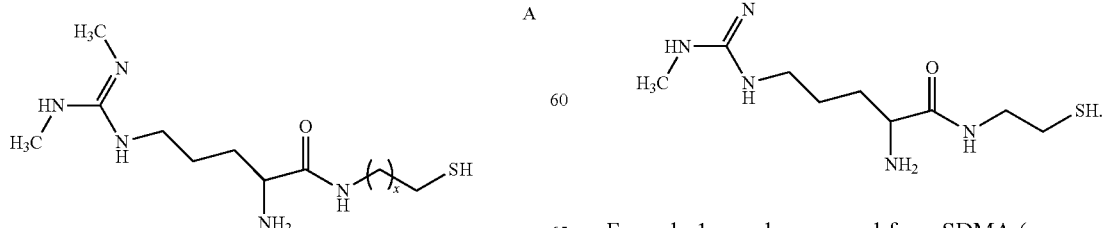

Formula 1 may be prepared from SDMA (commercially available from EMD Chemicals Inc. of Gibbstown, N.J.) by the following illustrative synthetic scheme (1):

Scheme 1

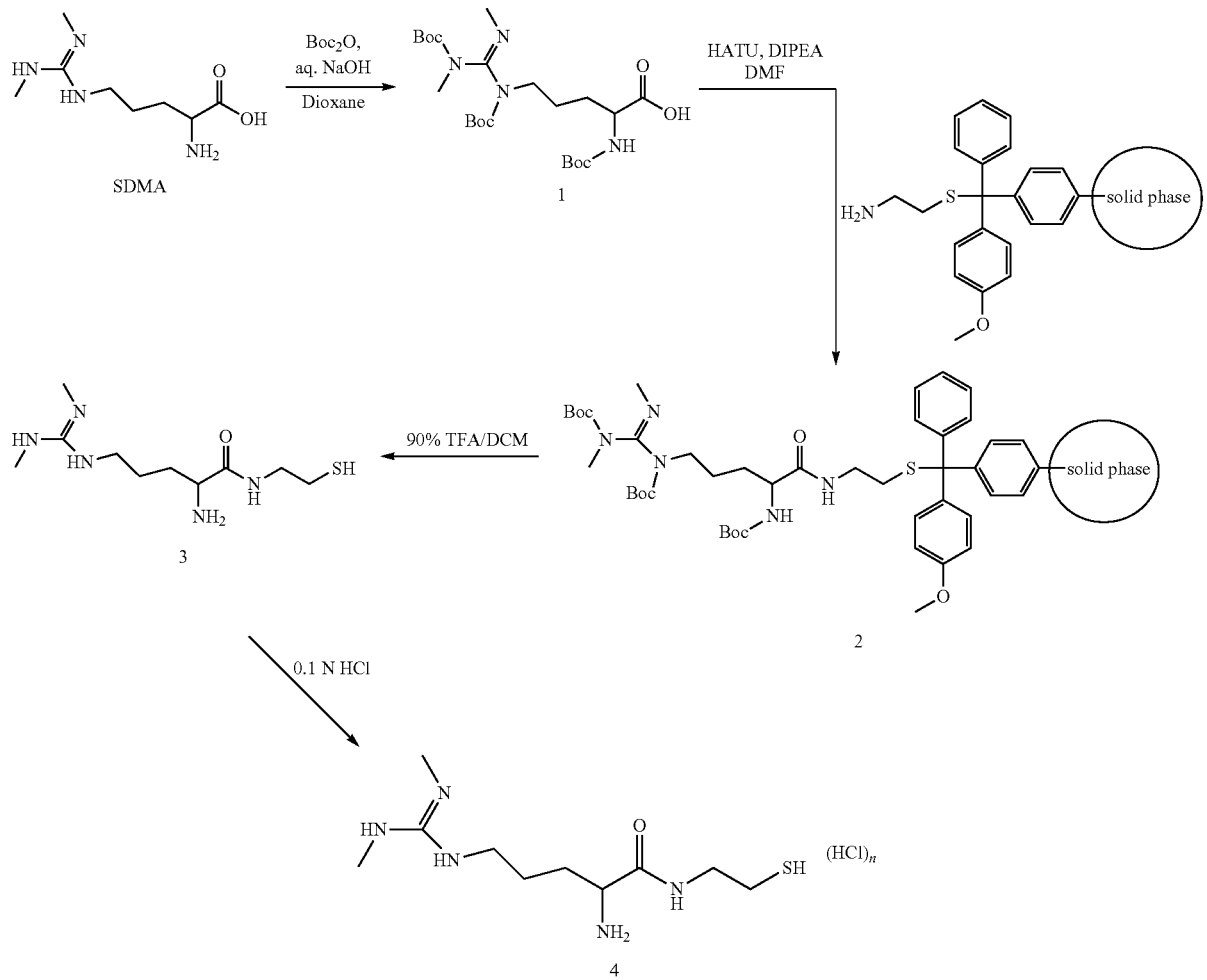

The primary and secondary amino groups of SDMA are protected by reacting SDMA with di-tert-butyldicarbonate (Boc$_2$O). The resulting tert-butoxycarbonyl (BOC) protected SDMA ((Boc$_3$)-SDMA, 1) is then linked to a resin. For example, the (Boc$_3$)-SDMA (1) can be linked to a cysteamine-4-methoxy trityl resin (EMD Chemicals, Inc., Gibbstown, N.J.) by contacting the (Boc$_3$)-SDMA (1) with the resin in the presence of 2-(1H-7-azabenzotriazol-1-yl)-1,1,3,3-tetramethyl uranium hexafluorophosphate methanamininium (HATU) and N,N-diisopropylethylamine (DIPEA) in dimethyl formamide (DMF) to provide resin bound (Boc$_3$)-SDMA cystamide (2). The BOC protecting groups on the resin bound (Boc$_3$)-SDMA cystamide (2) are removed and the resulting resin bound SDMA cystamide cleaved from the resin using, for example, trifluoroacetic acid in dichloromethane, to provide SDMA cystamide (3), which was converted to the hydrochloride salt (4) by reaction with hydrochloric acid.

Figure 5:
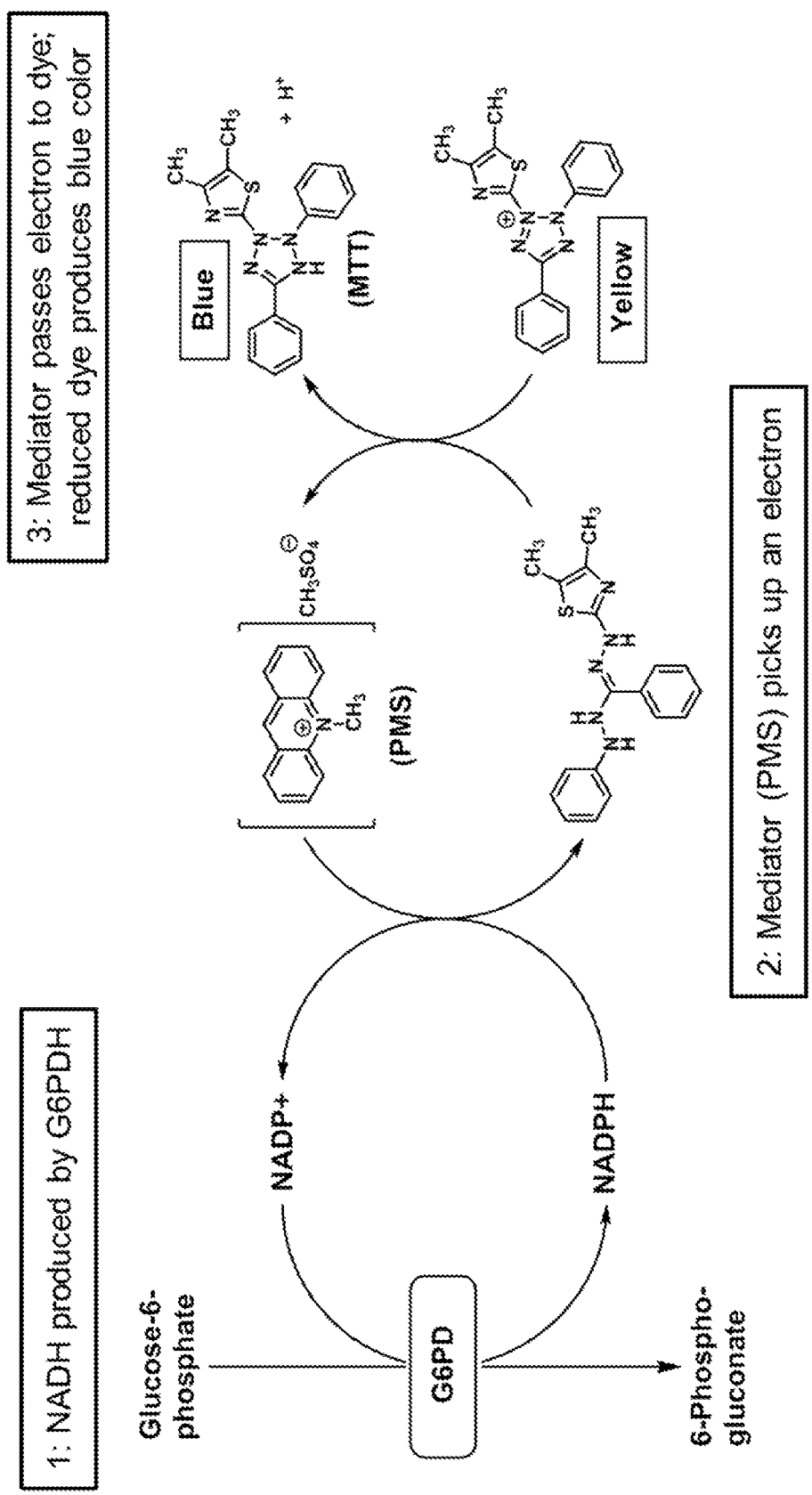
FIG. 5 is a schematic representation of a mediator-dye reaction mechanism wherein a mediator passes an electron to a dye in order to reduce the dye and shift the absorbance of the dye.

Traditional EMIT® assays measure the accumulation of NADH (or NADPH) by monitoring absorbance at 340 nm. In another embodiment of the disclosure, the addition of a color changing dye and an electron mediator to the reagents can allow absorbance to be measured at an absorbance other than 340 nm. In one particular example, the dye is 3-(4,5-dimethylthiazol-2-yl)-2,5-diphenyltetrazolium bromide (MTT) and the mediator is 1-methoxy phenazine methosulfate (PMS). As depicted in FIG. 5, the PMS picks up an electron from NADP and transfers it to the MTT, which reduces the MTT to provide for absorbance at approximately 650 nm.

Anti-SDMA antibodies may be polyclonal or monoclonal as described in U.S. Pat. No. 8,481,690. Methods of producing polyclonal and monoclonal antibodies within the skill in the art. In one embodiment, the antibody is a monoclonal antibody raised against a SDMA-KLH conjugate having the following structure:

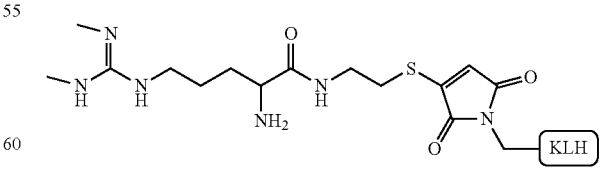

In various aspects, the anti-SDMA antibodies used in the modified assay of the disclosure can have high specificity for SDMA and no or substantially no cross-reactivity with one or more compounds selected from the group consisting of asymmetrical dimethylarginine (ADMA), L-arginine, and N-methylarginine. For example, the anti-SDMA antibody exhibit a reactivity for a ADMA, L-arginine, and N-methylarginine that is less than 25%, less than 20%, less than 15%, less than 10%, less than 5%, or less than 1% of the reactivity exhibited towards SDMA under a particular set of assay conditions.

All of the above described components may be used in a method for determining the presence or amount of free SDMA in a sample. For example, the method includes contacting the sample with an anti-SDMA antibody, a conjugate including SDMA and G6PDH, and a substrate(s) including NAD and G6P. As described herein the rate of conversion of NAD to NADH, is measured and compared to a standard curve to determine the presence or amount of SDMA in the sample. The SDMA is conjugated to the G6PDH with a 5-15 atom linker (2-10 Angstroms) as described herein. The anti-SDMA antibody may be monoclonal antibody that has no reactivity or substantially no reactivity for ADMA, L-arginine, and N-methylarginine In yet another embodiment, the disclosure is directed to a method for determining SDMA in a sample that includes derivatizing free SDMA and using an antibody directed to the derivative. For example, U.S. Patent Publication 2004/0214252, which is incorporated by reference herein in its entirety, describes a method for modification of the guanidino nitrogens of SDMA and antibodies to the modified SDMA. Accordingly, in one embodiment, the SDMA in a sample is modified prior to determination in the method according to the disclosure herein. In this embodiment, the anti-SDMA antibody should bind to both the modified SDMA and the SDMA of the conjugate, which may also be modified, with sufficient affinity to provide a suitable assay.

EXAMPLES

Example 1: Preparation of Stripped Serum

Untreated commercial canine serum (500 mL) was loaded to a two foot SNAKESKIN™ Dialysis tube (3.5 K MWCO, 35 mm Dry I.D.)(Thermo Scientific) and dialyzed against PBS buffer (20 L) with 20 g carbon powder at 4° C. for at least six hours. The process was repeated three times by changing buffer and carbon.

The SDMA concentration in the serum was measured by LC/MS before and after dialysis. In the serum before dialysis, SDMA was 9.89 μg/dL. After dialysis, SDMA was 0.02 μg/dL.

The charcoaled stripped canine serum was stored at −80° C. for use.

Example 2: SDMA Standards Preparation

SDMA.HCl (ChemBio) was dissolved in deionized water to a final concentration of SDMA of 1000 μg/ml. 200 μl of the SDMA aqueous solution was added into 10 ml of the stripped serum for final stock solution having an SDMA concentration of 20 μg/ml. The solution was stored at −80° C. 280 μl of the SDMA stock solution was transferred into 10 ml of stripped serum to prepare standard SDMA at 56 μg/dL. Other SDMA standards were prepared by serially diluting the stock solution in stripped serum to provide solutions of 28.0, 14.0, 7.0, and 3.75 μl/dL. The standards may be validated by LC/MS.

Example 3: Preparation of Diluents

Diluent Formulations R1 and R2 contained the components identified in Table 4. Sodium oxamate is an optional component as described elsewhere herein.

TABLE 4

| Components | Diluents | |
|---|---|---|
| | R1 | R2 |
| BSA | 1% | 1% |
| PEG6000 | 160 uM | 160 uM |
| Brij-35 | 0.12% | 0.12% |
| NaCl | 0.3M | 0.3M |
| Mouse Serum | 1% | 1% |
| EDTA | 1 mM | 1 mM |
| Proclin150 | 0.4% | 0.4% |
| G6P | — | 2 mM |
| Tris | 0.05M | 0.1M |
| pH | 7.0 | 8.0 |
| Oxamate (optional) | 0.015M | 0.015M |

Diluent Preparation Protocols

R1 Diluent (1 L scale). The following components were added to 500 ml of deionized water:
10 g of BSA
50 ml of 1M TRIS, pH8.0
0.372 g of EDTA sodium
4 ml of Brij-35 (30%)
4 ml of Proclin 150
0.96 g of PEG 6000
17.6 g of NaCl
10 ml of mouse serum
1.665 g of Sodium Oxamate (optional)

The solution was mixed well using a stir bar on a slow speed. Once the powder is fully dissolved, the pH was adjusted to 7.0 with 10N NaOH or 3N HCl as needed. The solution was added to a graduated cylinder and brought to a final volume of 1 L using deionized water. After mixing well, the solution was gently mixed well, and filtered through a 0.2 μm cellulose nitride filter unit and stored at 4° C. prior to use.

R2 Diluent (1 L scale): The following components were added to 500 ml of deionized water:
10 g of BSA
100 ml of 1M TRIS, pH8.0
2 ml of 0.5M EDTA (pH8.0)
4 ml of Brij-35 (30%)
4 ml of Proclin 150
0.96 g of PEG 6000
17.6 g of NaCl
10 ml of mouse serum
G6P 0.56 g
1.665 g of Sodium Oxamate (optional)

The solution was mixed well using a stir bar on a slow speed. Once powder is fully dissolved, the pH was adjusted to 8.0 with 10N NaOH or 3N HCl as needed. The solution was added to a graduated cylinder and brought to a final volume of 1 L using deionized water. After mixing well, the solution was gently mixed well, and filtered through a 0.2 μm cellulose nitride filter unit and stored at 4° C. prior to use.

Example 4: Preparation of Assay Reagents

Preparation of R1 Reagent and R1 Blank

The R1 Reagent and R1 Blank contained NAD (35 mM), G6P (56 mM) in R1 diluent. The R1 Reagent also included antibody (10.5 μg/ml). G6P is a stabilizer for the conjugate and is optional.

The diluent and other materials were brought to room temperature before preparing reagents. A 2× substrate working solution (100 ml) was prepared by adding 4.644 g of NAD, and 3.160 g of Sodium Glucose-6-Phosphate (G6P) to the R1 diluent. The powders were fully dissolved by gentle mixing and the pH was adjusted to 7.0 with 10M NaOH or 3 M HCl. The solution was added to a graduated cylinder and additional R1 Diluent was added to give a final volume of 100 mL. The solution was mixed well by gently rotating on a roller and filtered through a 0.2 µm cellulose nitride filter unit 4× antibody working solution (25 ml) was prepared by pre-diluting antibody stock (6.6 mg/ml) into R1 Diluent 1:10 fold to give an antibody solution of 660 µg/ml. 1.59 ml of pre-diluted antibody solution (660 µg/ml) was added into 23.41 ml of R1 Diluent to prepare antibody working solution (4×) at concentration 42 µg/ml.

The R1 Reagent was prepared by mixing 40 ml of substrate working solution (2×), 20 ml of antibody working solution (4×), and 20 ml of R1 Diluent. The solution was gently mixed, covered with aluminum foil, and stored at 4° C. prior to use.

R1 Blank was prepared by mixing 40 ml of substrate working solution (2×) and 40 ml R1 Diluent. The solution was gently mixed, covered with aluminum foil, and stored at 4° C. prior to use.

Preparation of R2 Reagent and R2 Blank

The R2 Reagent contained the SDMA-G6PDH conjugate (0.42 µg/ml) in R2 Diluent. The R2 Blank contained the SDMA-G6PDH conjugate (0.014 µg/mL) in R2 Diluent.

0.3 ml of conjugate stock (Lot #5616-80-2, 770 µg/ml) was added to 29.7 ml of R2 Diluent to pre-dilute the conjugate 1:100 fold giving a final concentration of 7.7 µg/ml 21.8 ml of the pre-diluted conjugate solution was added into 378.2 ml of R2 Diluent to prepare R2 Reagent.

0.73 ml of the pre-diluted conjugate solution was added into 399.27 ml R2 Blank to prepare R2 Blank.

The solutions were mixed well and stored at 4° C. prior to use.

Example 5: Preparation of SDMA analog N, N'-dimethylarginine thiol (SDMA-SH)

Materials:
Cysteamine 4-methoxytrityl resin: Loading 0.7 mmol/g resin and 200-400 mesh co-polymer matrix (Novabiochem).
Fmoc-SDMA(Boc)2ONa: MW 624.7, purity 95%, (Novabiochem)
HATU: MW 380.3 (Novabiochem).
N, N-Diisopropyl ethylamine: purified by redistillation, 99.5% from Sigma.
DMF (anhydrous): Purity 99.8% from Sigma.
Piperidine: 20% in anhydrous DMF.
Procedure:
To a 20 mL vial was added cysteamine 4-methoxytrityl resin (1.2 g, 0.46 mmol), Fmoc-SDMA(Boc)2ONa (0.9 g, 1.4 mmol, 3.0 equivalents), HATU (0.54 g, 1.4 mmol, 3.0 equivalents), diisopropyl ethylamine (0.4 mL, 2.3 mmol, 5.0 equivalents) and anhydrous DMF (18 mL). The mixture was capped and inverted at room temperature for 16 hours. The liquid was removed from the vial using a glass pipet. The resin was then washed with DMF (18 mL, 4 times) then methanol (18 mL, 4 times). The resin was inverted in 20% piperidine in DMF at room temperature for 15 minutes (18 mL, 3 times). The resin was then washed with DMF (18 mL, 4 times) then methanol (18 mL, 4 times) and dried on the lyophilizer for 1 hour. The yellow/light pink resin can then be stored at 4° C. or cleaved to give SDMA-SH.

To cleave the SDMA-SH from the resin (50 mg) was inverted in trifluoroacetic acid (3 mL) at room temperature for 1 hour. The dark red slurry is then filtered and rinsed with acetonitrile (1 mL) to give a clear yellow solution. The solution is then lyophilized to give SDMA-SH (7 mg) as a thick yellow oil. Due to oxidation of the thiol, the compound should be used immediately or stored at −80° C. (storage at −80° C. results in <10% oxidation after 2 months). SDMA-SH (Formula 1) was confirmed by LC/MS and NMR.

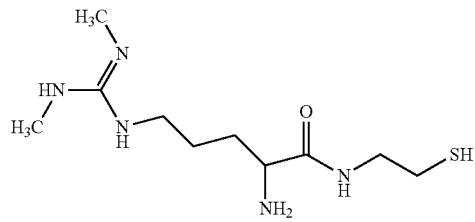 [SMILES: C/N=C(\NC)NCCCC(N)C(=O)NCCS]

Formula 1

Example 6: Conjugation of SDMA and G6PDH

Conjugates of SDMA and G6PDH were prepared by conjugating the SDMA analog SDMA-SH with G6PDH activated with either SIA, SBAP or SMCC in the presence of NAD and G6P. The length of the linker between the SDMA and G6PDH could be varied by selecting the reagent used for activation as shown in FIGS. 2, 3 and 4.

Enzyme Preactivation with SIA:

One vial of Glucose-6-phosphate dehydrogenase (G6PDH) (12 mg) was dissolved in 3 ml MES buffer (50 mM, pH8 0.0) and rotated for 1 hour to ensure that the enzyme is fully dissolved. The enzyme solution was kept on ice until needed. An additional 4.5 ml MES buffer (50 mM, pH 8.0) was added to the enzyme solution, mixed well through vortexing (5 seconds) and kept on ice for 10 minutes. 100 mg G6P was dissolve in 1ml deionized water and on ice for 10 min. 200 mg NADH was dissolve in 1 ml deionized water and keep on ice for 10 min. 0.68 ml G6P solution and 0.34 ml NADH solution were added to the enzyme solution, mixed well through vortexing (5 seconds) and kept on ice for 10 min. One vial of SIA (50 mg) was dissolved in 0.5 ml DMSO (100 mg/ml). 0.14 ml of the SIA solution was added to the enzyme solution, mixed well through vortexing (5 seconds), covered with aluminum foil, and rotated at room temperature for 2 hours. The solution was transferred to a G2 Slide-A-Lyzer Dialysis Cassette and dialyzed for five hours against PBS buffer (4 L) at 4° C. in the dark. The buffer was changed to fresh PBS (4 L) and the solution was dialyzed at 4° C. overnight in the dark. The dialysis buffer was changed to MES (4 L, 25 mM, pH 8.0) and the solution was dialyzed for 3 hours at 4° C. 12.5 ml of the enzyme solution was removed from the dialysis cassette and 0.32 ml MES buffer (1M, pH8.0) and 0.32 ml EDTA (0.2M, pH8.0) was added to bring the final concentration of the solution to 50 mM MES and 5 mM EDTA. If necessary, if the enzyme solution is less than 12.5 ml, the volumes of MES and EDTA may be adjusted accordingly. The solution was degassed with argon for 5 minutes.

Enzyme Preactivation with SBAP:

To 2 mg of G6PDH in 1 ml MES buffer (50 mM, pH8.0), 11.3 mg G6P and 16.8 mg NADH was added, mixed well and kept on ice for 10 min. SBPA (50 mg) was dissolved in 0.5 ml DMSO (100 mg/ml). 0.025 ml SBAP was added to the enzyme solution, mixed well through vortexing (5 seconds), covered in aluminum foil, and rotated at room temperature for 2 hours. The solution was transferred to a G2 Slide-A-Lyzer Dialysis Cassette and dialyzed for five hours against PBS buffer (2 L) at 4° C. in the dark. The buffer was changed to fresh PBS (2 L), and the solution was dialyzed at 4° C. overnight in the dark. The dialysis buffer was changed to MES (2 L, 25 mM, pH 8.0) and the solution was dialyzed for 3 hours at 4° C. 2.5 ml of enzyme solution was removed from the dialysis cassette and 0.060 ml MES buffer (1M, pH8.0) and 0.025 ml EDTA (0.5M, pH8.0) was added to bring the final concentration of the solution to 50 mM MES and 5 mM EDTA.

Enzyme Preactivation with SMCC:

To 2 mg of G6PDH in 1 ml MES buffer (50 mM, pH8.0), 11.3 mg G6P and 16.8 mg NADH was added, mixed well and kept on ice for 10 min. 50 mg Sulfosuccinimidyl-4-(N-maleimidomethyl)cyclohexane-1-carboxylate (SMCC) was dissolved in 0.5 ml DMSO (100 mg/ml). 0.035 ml SMCC solution was added to the enzyme solution, mixed well through vortexing (5 seconds), covered in aluminum foil and rotated at room temperature for 2 hours. The solution was transferred to a G2 Slide-A-Lyzer Dialysis Cassette and dialyzed for five hours against PBS buffer (2 L) at 4° C. in the dark. The buffer was changed to fresh PBS (2 L), and the solution was dialyzed the solution at 4° C. overnight in the dark. Change the dialysis buffer to MES (2 L, 25 mM, pH 8.0) for 3 hours at 4° C. 2.5 ml of enzyme solution was removed from the dialysis cassette and 0.060 ml MES buffer (1M, pH8.0) and 0.025 ml EDTA (0.5M, pH8.0) was added to bring the final concentration of the solution to 50 mM MES and 5 mM EDTA.

Conjugation of SDMA and preactivated G6PDH: The freshly prepared SDMA-SH (Formula 1) was added to the preactivated enzyme solutions in the following amounts: 0.35 ml (100 mg/ml) for SIA-activated G6PDH and 0.065 ml (100 mg/ml) for SBAP or SMCC-activated G6PDH. The solutions were mixed well, and the mixture was rotated for 36 hours at 4° C. The reaction mixture was dialyzed (3 or 4 cycles) using a G2 Slide-A-Lyzer Dialysis Cassette (Thermo Scientific), against PBS (2 or 4 L) at 4° C. The SDMA-enzyme conjugate solution was equilibrated by dialyzing against Tris HCl buffer (25 mM, pH 8.0) for 4 hours at 4° C. The solution was filtered using a 0.45 μm centrifugal filter (1500*g for 10 minutes).

Table 5 shows the linker length and activity of each of the conjugates and ability of the antibody to inhibit G6PDH of the conjugates. Linker length does not include the non-native nitrogen in the SDMA derivative of Formula 1. Preactivation of G6PDH in the presence of SIA resulted in better enzyme activity than conjugates prepared with SBAP or SMCC.

TABLE 5

| Conjugates | Linker Length (atoms) | Linker Length (Angstroms) | Activity (%) | Inhibition (%) |
|---|---|---|---|---|
| SDMA-SMCC-G6PDH | 12 | 13.0 | 1.5 | 25 |
| SDMA-SBPA-G6PDH | 9 | 10.1 | 10.8 | 40 |
| SDMA-SIA-G6PDH | 5 | 6.4 | 30 | 70 |

Example 7: Preparation of Anti-SDMA Monoclonal Antibody

Methods of producing monoclonal antibodies are within the skill in the art. In one embodiment, the antibody is a monoclonal antibody raised against a SDMA-KLH conjugate having the following structure:

Purification of the anti-SDMA antibody was conducted as follows:

Materials:
2×2 L of anti-SDMA
Reverse Phase (rPA) column (5 ml) (GE Healthcare) dedicated for anti-SDMA IgG purification
Pierce IgG Purification Buffers
  IgG Binding buffer
  IgG Low pH Elution buffer
PBS, pH 7.4 for dialysis
  2×4 L@4 C
Protocol:
rPA column (5 ml) was equilibrated in binding buffer at 3 ml/min
  1. flow monitored by OD 280 nm
1000 ml of anti-SDMA was diluted in equal volume of Pierce IgG Binding buffer
  1. Process repeated for additional 1000 ml
Diluted anti-SDMA loaded on rPA column at 6 ml/min
  1. OD monitored by 280 nM
rPA column washed with PBS/IgG Binding buffer 1:1 @ 3 ml/min until
  1. OD 280 nM reached baseline
anti-SDMA IgG was eluted using IgG Low pH Elution buffer @ 3 min/ml
  1. peak was collected manually
anti-SDMA IgG was immediately dialyzed against 2 changes of 4 L of PBS
  1. 30 ml 10k MWCO cassette(s)
  2. Volume pooled and OD 280 nm used to determine IgG concentration The antibody was analyzed by SDS Page, SEC and a plate-based immunoassay as described in U.S. Pat. No. 8,481,690.

Example 8: Assay Procedures

The modified assay of the disclosure was carried out for SDMA in canine, feline and human samples.

Reagents components are shown in Table 5A

TABLE 5A

| Component/Assay Reagent | Color Assay R1 | Color Assay R2 | Blank Assay R1 | Blank Assay R2 |
|---|---|---|---|---|
| Antibody (μg/mL) | 6.56 | 0 | 0 | 0 |
| G6P (mM) | 56 | 2 | 56 | 2 |
| NAD (mM) | 35 | 0 | 35 | 0 |
| SDMA-G6PDH (μg/mL) | 0 | 0.42 | 0 | 0.014 |

Pipetting volumes for reagents prepared as described above were identical for the Color Assay and Blank Assay:

| | Volume (μl) |
|---|---|
| Sample or Calibrator | 10 |
| R1 | 40 |
| R2 | 125 |

Color and Blank Assays for sample and calibrators and related calculations were conducted on a Beckman AU680® automated analyzer. Calibration standards containing SDMA at 56.0, 28.0, 14.0, 7.0, and 3.75 and 0 μg/dL in calibrator matrix (stripped canine serum) were used for both cats and dogs. The analyzer was programmed to conduct the Color and Blank Assays as follows: the sample and calibrators were added to reagent R1 and incubated for 3-4 minutes before the addition of R2. The OD was measured at 340 nm using starting at approximately 36 seconds following the addition of R2. Absorbance was measured every 18 seconds for 4 additional 18 second cycles. The absorbance value of the calibrator matrix (0 μg/dL SDMA) was subtracted from each of the measurements used to calculate the reaction rates (change of absorbance/min) of the Color and Blank assays to provide normalized Color and Blank reaction rates.

In order to determine the rate for a standard curve, the normalized rate for each calibrator from the Blank Assay was subtracted from the normalized rates for each calibrator in the Color Assays. Sample SDMA concentration was determined by subtracting the normalized rate for the sample in the Blank assay from the normalized rate for the sample in the Color assay to provide a final sample reaction rate, which was compared to the final standard curve.

Table 6 shows the results of the SDMA assays for feline and canine serum using the Color Assay alone ("without subtraction") and when the Blank Assay rate is subtracted from the Color Assay rate ("with subtraction"). Sample Bias reflects the difference between the LC/MS result and the result using the above procedure.

TABLE 6

| Species | LC/MS [SDMA] (μg/dL) | SDMA Assay with subtraction | HSDMA Assay without subtraction | Sample Bias with subtraction | Sample Bias without subtraction |
|---|---|---|---|---|---|
| Feline | 9.7 | 10.4 | 12.6 | 0.7 | 2.8 |
| Feline | 19.1 | 19.8 | 31.4 | 0.7 | 12.3 |
| Canine | 34.1 | 35.0 | 37.4 | 0.9 | 3.3 |
| Feline | 43.3 | 42.1 | 49.7 | −1.2 | 6.4 |
| Canine | 10.4 | 10.3 | 12.4 | −0.1 | 2.1 |
| Canine | 6.6 | 7.3 | 8.0 | 0.7 | 1.4 |
| Feline | 18.4 | 18.9 | 25.8 | 0.5 | 7.4 |
| Canine | 6.6 | 5.6 | 8.2 | −1.0 | 1.6 |
| Feline | 10.8 | 10.6 | 17.9 | −0.2 | 7.2 |
| Feline | 9.9 | 10.0 | 15.9 | 0.1 | 5.9 |
| MEAN | | | | 0.1 | 5.0 |

Table 7 shows a calibration curves prepared with and without subtraction using known amounts of SDMA in stripped canine serum. Similar curves were prepared for the other species.

TABLE 7

| SDMA (μg/dL) | With Subtraction (μg/dL) | Without Subtraction (μg/dL) |
|---|---|---|
| 0.1 | 0.0 | 0.0 |
| 5.1 | 4.3 | 2.8 |
| 14.8 | 17.6 | 16.2 |
| 28.4 | 38.0 | 36.6 |
| 59.9 | 75.5 | 73.9 |
| 97.9 | 116.0 | 114.3 |

Figure 6:
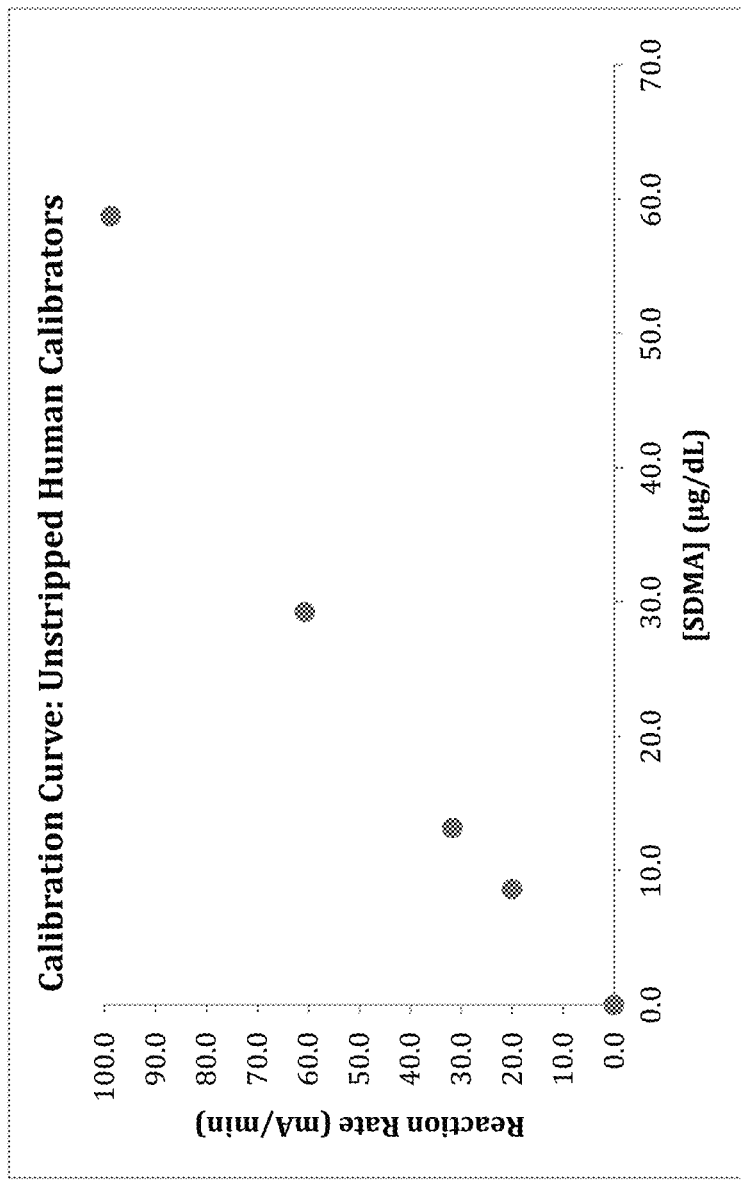
FIG. 6 shows a calibration curve for SDMA spiked into human sera and analyzed according to the method of the disclosure.

Table 8 shows the values for the calibration curve show in FIG. 6 using unstripped human sera spiked with SDMA using the Rate assay procedure described above (i.e., Color and Blank Assays with subtraction).

TABLE 8

| [SDMA] (μg/dL) | Reaction Rate (ΔA/min) |
|---|---|
| 0.0 | 0.0 |
| 8.6 | 20.0 |
| 13.2 | 31.7 |
| 29.3 | 60.7 |
| 58.8 | 98.8 |

The curve was used to determine the concentration in normal and chronic kidney disease human serum samples as shown in FIG. 1.

Example 9: Use of Enzyme Inhibitors

Lactate dehydrogenase inhibitor sodium oxamate was added to the blank reagents diluent and reagents as described above in Example 3. Use of the inhibitor can improve the accurate of the assay as shown in Table 9.

TABLE 9

| Species | LC/MS [SDMA] (μg/dL) | Assay Result with no inhibitor | Assay Result with sodium oxamate | Bias without inhibitor | Bias with inhibitor |
|---|---|---|---|---|---|
| Feline | 35.5 | 37.3 | 35.8 | 1.8 | 0.3 |
| Feline | 12.0 | 14.1 | 12.1 | 2.1 | 0.1 |
| Canine | 10.7 | 12.7 | 10.9 | 2.0 | 0.2 |
| Feline | 9.6 | 11.9 | 9.3 | 2.3 | −0.3 |
| Feline | 6.4 | 3.9 | 6.2 | −2.5 | −0.2 |
| Canine | 7.9 | 9.7 | 7.9 | 1.8 | 0.0 |
| Canine | 8.6 | 9.7 | 8.5 | 1.1 | −0.1 |
| Canine | 12.4 | 13.5 | 12.6 | 1.1 | 0.2 |
| Feline | 14.0 | 15.0 | 14.1 | 1.0 | 0.1 |
| Canine | 7.7 | 9.1 | 7.8 | 1.4 | 0.1 |
| MEAN | | | | 1.2 | 0.0 |

In this example, the standard curve for canine serum was prepared with and without sodium oxamate as shown in in Table 10. A similar curve can be prepared for other species.

TABLE 10

| SDMA (μg/dL) | Without Oxamate | With Oxamate |
|---|---|---|
| 0.1 | 0.0 | 0.0 |
| 5.1 | 4.3 | 4.1 |
| 14.8 | 17.6 | 18.0 |
| 28.4 | 38.0 | 37.9 |
| 59.9 | 75.5 | 73.7 |
| 97.9 | 116.0 | 116.0 |

Example 10: Testing Human Serum Samples with Stripped and Unstripped Human Serum Calibrators The recovery of SDMA in human serum samples using endogenous and charcoal stripped human serum as calibrator matrices was determined. The data collected in this experiment can be used to prepare calibration curves with Rate and Fixed calibration methods.

Assay reagents were prepared as shown in Table 11.

TABLE 11

| Component | Reagent 1 | Reagent 2 |
|---|---|---|
| Tris-HCl | 50 mM, pH 7.0 | 100 mM, pH 8.0 |
| EDTA | 1.3 mM | 1.3 mM |
| NaCl | 0.3M | 0.3M |
| Brij 35 | 0.14% | 0.14% |
| PEG 6000 | 0.16 mM | 0.16 mM |
| Proclin | 0.2% | 0.2% |
| Mouse serum | 1% | 1% |
| Bovine serum albumin | 1% | 1% |
| G6P | 56 mM | 2 mM |
| NAD | 35 mM | 0 mM |

The anti-SDMA mAb was prepared as in Example 7 and used at 1.5 µg/mL in-assay concentration The SDMA-G6PDH was prepared as in Example 6 and used at 0.3 µg/mL in-assay concentration Calibrators were prepared with charcoal stripped human serum with the following SDMA concentrations (m/dL): 0.0, 4.7, 15.0, 29.0, 59.0 and 111.0 determined by LC/MS.

The rate method was conducted according to Example 8.

In the fixed method, the Beckman instrument was set to measure a change in absorbance at 340 nm between one minute and three minutes after the start of the reaction.

Figure 7:
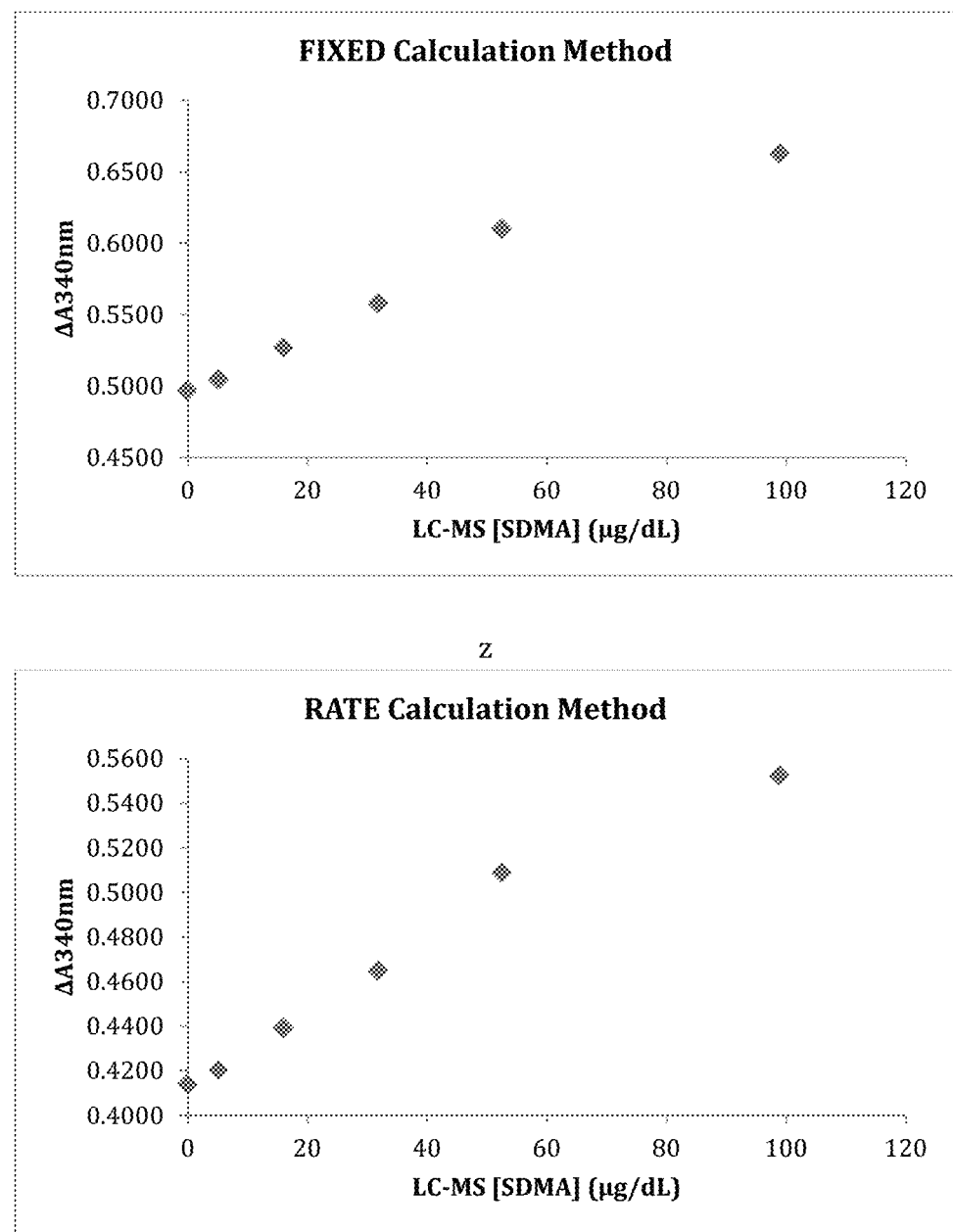
FIG. 7 shows calibration curves for SDMA spiked in human serum and analyzed according to a fixed calculation method and the rate calculation method of the disclosure.

Results of the Fixed and Rate calculation methods for the determination of SDMA concentration are shown in FIG. 7.

Example 11: Unstripped Human Calibrator Dose with Buffer Calibrators

An SDMA assay was calibrated using buffer-based calibrators (0, 6, 11, 24, 46, and 95 ug/dL SDMA in PBS buffer with 1% BSA) and used to test unstripped human serum standards to determine recovery. This experiment used the Fixed method to calculate the change in absorbance at 340 nm at instrument cycles 12 and 16, where each cycle is 18 seconds (T1=216 seconds, T2=288 second). The absorbance from a reagent blank (diH2O) was not subtracted from the net absorbance.

Figure 8:
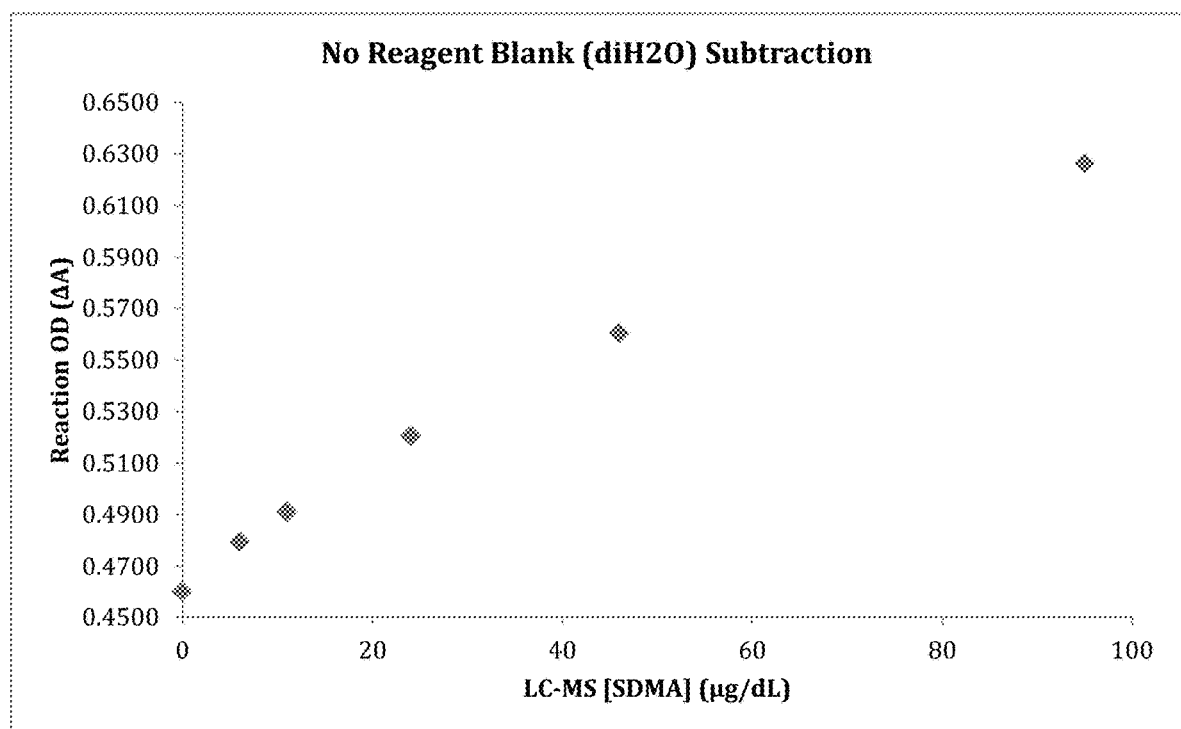
FIG. 8 shows the results of an assay for known concentrations of SDMA conducted according to the disclosure without subtracting for background signal.

The assay was run as shown in Example 9. Results are shown in FIG. 8.

Example 12: Comparison of Manual and Automated Background Subtraction

The automated background subtraction methods on-board the Beckman AU680® analyzer were tested to determine the effectiveness of on-board solutions. An SDMA assay was run on board the instruction and the assay was run separately and results calculated using offline methods as a control.

Charcoal stripped canine serum calibrators were prepared as in Example 1. Reagents components are shown in Table 12.

TABLE 12

| Component | Reagent 1 | Reagent 2 | R1 Blank | R2 Blank |
|---|---|---|---|---|
| NAD (mM) | 5 | 0 | 5 | 0 |
| G6P (mM) | 8 | 0 | 8 | 0 |
| SDMA-mAb (µg/mL) | 2 | 0 | 0 | 0 |
| SDMA-G6PDH (µg/mL) | 0 | 0.4 | 0 | 0.004 |

Reaction volumes were as follows:

Sample volume: 170 µL

Reagent 1 volume: 250 µL

Reagent 2 volume: 1250 µL

Color and Blank assay not linked on-board the analyzer. Data was generated for each assay separately and processed off the instrument. Blank assay reaction OD is subtracted from the Color assay reaction OD for calibrators and samples. A curve is fitted to the calibration data and the equation of the best fit curve is used to determine sample concentration from the subtracted reaction OD.

Table 13 shows the net change in absorbance for the calibrators in the Fixed reaction method:

TABLE 13

| Calibrator | LC-MS [SDMA] (µg/dL) | ΔA340 nm Color | Blank | Net |
|---|---|---|---|---|
| Cal 0 | 0.0 | 0.5878 | 0.0082 | 0.5796 |
| Cal 0 | 0.0 | 0.5842 | 0.0081 | 0.5761 |
| Cal 1 | 4.7 | 0.6018 | 0.0081 | 0.5937 |
| Cal 1 | 4.7 | 0.6017 | 0.0076 | 0.5941 |
| Cal 2 | 15.0 | 0.6530 | 0.0082 | 0.6448 |
| Cal 2 | 15.0 | 0.6491 | 0.0071 | 0.6420 |
| Cal 3 | 29.0 | 0.7043 | 0.0067 | 0.6976 |
| Cal 3 | 29.0 | 0.6957 | 0.0064 | 0.6893 |
| Cal 4 | 59.0 | 0.7674 | 0.0062 | 0.7613 |
| Cal 4 | 59.0 | 0.7721 | 0.0072 | 0.7649 |
| Cal 5 | 111.0 | 0.8503 | 0.0077 | 0.8426 |
| Cal 5 | 111.0 | 0.8479 | 0.0075 | 0.8404 |

Table 14 shows the measurement of SDMA in a sample using a standard curve generated from the calibrators shown in Table 13.

TABLE 14

| Sample | LC-MS [SDMA] (µg/dL) | Color | Blank | Net | Assay Dose (µg/dL) |
|---|---|---|---|---|---|
| 1 | 8.8 | 0.6634 | 0.0498 | 0.6137 | 8.3 |
| 2 | 8.3 | 0.6439 | 0.0298 | 0.6141 | 8.4 |

Example 12: Analysis of Calibrator Matrices from Different Species

Calibrator sets made from pooled serum of varied animal species were analyzed to determine the robustness of the SDMA assays when using calibrators with serum from different species.

Assays for human SDMA were performed using the Fixed method as in Example 10 on calibrators made with stripped or endogenous (unstripped) serum from dogs, cats, and horses. The results of the assays are show in FIGS. 8, 9 and 10

Example 13: Buffer-Based Calibration

Figure 12:
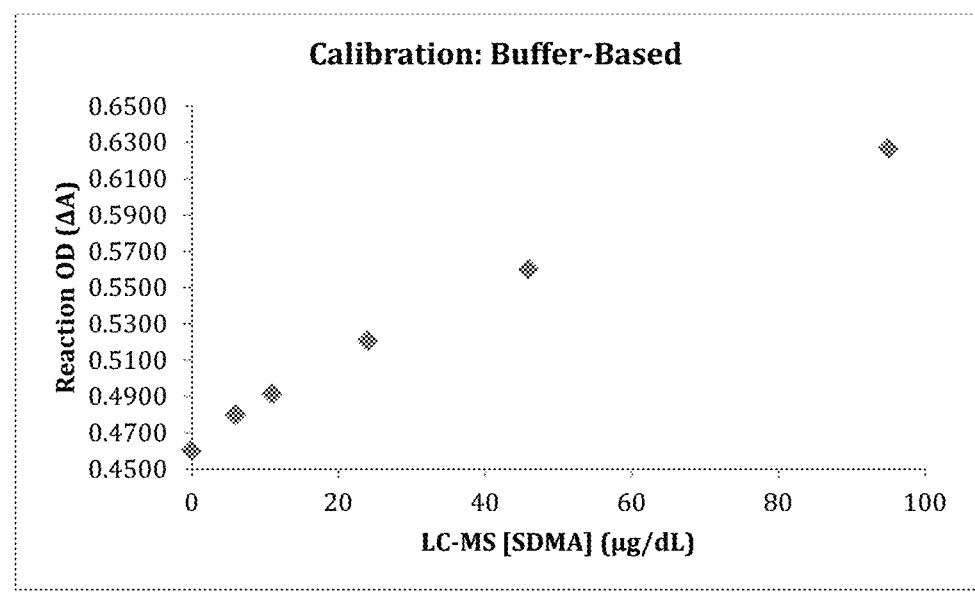
FIG. 12 shows the results of an SDMA assay according to the disclosure using a buffer-based calibrator.

A calibration curve was made using 1% BSA in PBS as a calibration matrix for the calibration concentrations in Table 13. The results are shown in FIG. 12.

Example 14: SDMA Assay without Conjugate Added to Blank Reagents

SDMA assays were run using the Rate procedure of Example 8 with the reagent concentrations of Table 5A, except that the conjugate was not added to R2. Assays were run on the Beckman analyzer. The results are shown in Table 15.

TABLE 15

| Species | Sample ID | [SDMA] LC/MS | Assay Dose (µg/dL) | Bias |
|---|---|---|---|---|
| Canine | 4865 | 7.0 | 7.5 | 0.49 |
| Canine | 4868 | 8.8 | 9.6 | 0.89 |
| Canine | 4941 | 7.7 | 8.3 | 0.63 |
| Canine | 4942 | 7.3 | 7.9 | 0.61 |

Although various specific embodiments of the present disclosure have been described herein, it is to be understood that the disclosure is not limited to those precise embodiments and that various changes or modifications can be affected therein by one skilled in the art without departing from the scope and spirit of the disclosure.

The examples given above are merely illustrative and are not meant to be an exhaustive list of all possible embodiments, applications or modifications of the disclosure. Thus, various modifications and variations of the described methods and systems of the disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure which are obvious to those skilled in molecular biology, immunology, chemistry, biochemistry or in the relevant fields are intended to be within the scope of the appended claims.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

What is claimed is:

1. A conjugate comprising symmetrical dimethyl arginine (SDMA) conjugated to glucose-6-phosphate dehydrogenase (G6PDH) through a 5 to 9 atom linker.

2. A conjugate of claim 1, wherein the SDMA is conjugated to the G6PDH through a 5 atom linker.

3. A conjugate of claim 1, wherein the SDMA is conjugated to the G6PDH through a 9 atom linker.

4. A conjugate of claim 1, wherein the SDMA and the linker form a group of the formula

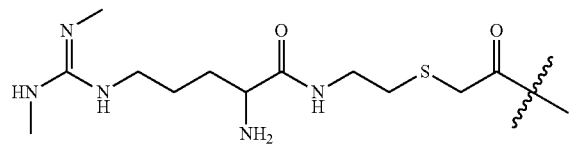

5. A conjugate of claim 1, wherein the SDMA and the linker form a group of the formula

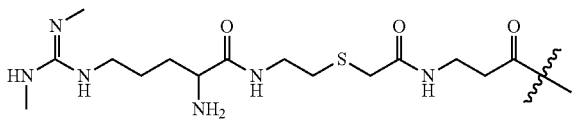

6. A reaction mixture comprising the conjugate of claim 1 and a sample suspected of comprising SDMA.

* * * * *